(12) United States Patent
Ling et al.

(10) Patent No.: US 9,950,080 B2
(45) Date of Patent: Apr. 24, 2018

(54) AMPHIPHILIC CYCLODEXTRIN-BASED GLYCODENDRIMERS

(71) Applicant: UTI Limited Partnership, Calgary (CA)

(72) Inventors: Chang-Chun Ling, Calgary (CA); Lina Cui, Mountain View, CA (US); Ramprasad Ghosh, Halifax (CA); Ping Zhang, Calgary (CA); Aixia Wang, Calgary (CA)

(73) Assignee: UTI Limited Partnership, Calgary Alberta (CA)

( * ) Notice: Subject to any disclaimer, the term of this patent is extended or adjusted under 35 U.S.C. 154(b) by 0 days.

(21) Appl. No.: 15/026,558

(22) PCT Filed: Oct. 1, 2014

(86) PCT No.: PCT/CA2014/050944
§ 371 (c)(1),
(2) Date: Mar. 31, 2016

(87) PCT Pub. No.: WO2015/048897
PCT Pub. Date: Apr. 9, 2015

(65) Prior Publication Data
US 2016/0367700 A1    Dec. 22, 2016

Related U.S. Application Data

(60) Provisional application No. 61/885,151, filed on Oct. 1, 2013.

(51) Int. Cl.
| | |
|---|---|
| *A61K 47/48* | (2006.01) |
| *A61K 9/107* | (2006.01) |
| *A61K 31/437* | (2006.01) |
| *C08B 37/16* | (2006.01) |
| *A61K 47/40* | (2006.01) |
| *C08L 5/16* | (2006.01) |
| *C08G 83/00* | (2006.01) |
| *A61K 47/08* | (2006.01) |
| *A61K 47/61* | (2017.01) |
| *A61K 47/69* | (2017.01) |

(52) U.S. Cl.
CPC ........ *A61K 47/48969* (2013.01); *A61K 9/107* (2013.01); *A61K 31/437* (2013.01); *A61K 47/08* (2013.01); *A61K 47/40* (2013.01); *A61K 47/61* (2017.08); *A61K 47/6951* (2017.08); *C08B 37/0012* (2013.01); *C08B 37/0015* (2013.01); *C08G 83/003* (2013.01); *C08L 5/16* (2013.01)

(58) Field of Classification Search
None
See application file for complete search history.

(56) References Cited

FOREIGN PATENT DOCUMENTS

| | | |
|---|---|---|
| CA | 2 406 823 A1 | 8/2001 |
| CA | 2 761 752 | * 10/2010 |
| WO | WO 2015/048897 A1 | 9/2015 |

OTHER PUBLICATIONS

Mendez-Ardoy et al. in Journal of Organic Chemistry 76, 5882-5894 (2011).*
Mendez-Ardoy et al. in Journal of Organic Chemistry 76, 5882-5894.*
Garcia Barrientos et al. in Synthesis 1057-1064 (2001).*
Vico, et al., "Multivalent Interaction of Cyclodextrin Vesicles, Carbohydrate Guests, and Lectins: A Kinetic Investigation," Langmuir, pp. 1391-1397 (2010).
Voskuhl, et al., "Sugar-Decorated Sugar Vesicles: Lectin-Carbohydrate Recognition at the Surface of Cyclodextrin Vesicles," Chemistry—A European Journal, pp. 2790-2796 (2010).
Mendez-Ardoy, et al., "B-Cyclodextrin-Based Polycationic Amphiphilic "Click" Clusters: Effect of Structural Modifications in Their DNA Complexing and Delivery Porperties," The Journal of Organic Chemistry, pp. 5882-5894 (2011).
International Search Report for International Application No. PCT/CA2014/050944, dated Dec. 12, 2014.
Written Opinion of the International Searching Authority for International Application No. PCT/CA2014/050944, dated Dec. 12, 2014.

* cited by examiner

Primary Examiner — Dennis Heyer
(74) Attorney, Agent, or Firm — Cook Alex Ltd.

(57) ABSTRACT

The present application provides an amphiphilic cyclodextrin-based compound of the formula I: R-G-D-A (I) wherein R is one or more hydrophilic groups; G is one or more linkers; D is a cyclodextrin, and A is one or more aliphatic groups. In certain embodiments, the hydrophilic group is a sugar such as lactose, the linker comprises —(CHR'CH$_2$O)$_n$— where R' is H or is an alkyl group substituted with —(CHR'CH$_2$O)$_n$— where n is 1 to 20, typically n=4; the cyclodextrin is a β-cyclodextrin comprising 7 subunits, and the aliphatic groups are C$_6$ alkyl groups. The compound can be used to enhance water solubility, bioavailability, cellular uptakes of active ingredients used in medicines, cosmetics and foods and other products, for detection, removal and immobilization of pathogenic organisms, toxins, and autoantibodies, and biomarkers on solid matrix, or for molecular biological techniques, such as ELISA, for example.

13 Claims, 37 Drawing Sheets

H. Parrot-Lopez, C.-C. Ling, P. Zhang, A. Baszkin, G. Albrecht, C. de Rango and A. W. Coleman, *J. Am. Chem. Soc.* 1992, 114, 5479-5480.

Figure 2 - Prior Art

A comparison of (a) saturated Nile Red in water, (b) Nile Red + Lactose_C6CD, and (c) Nile Red + Lactose_C12CD in water solutions. The fluorescence spectra of the above three solutions.

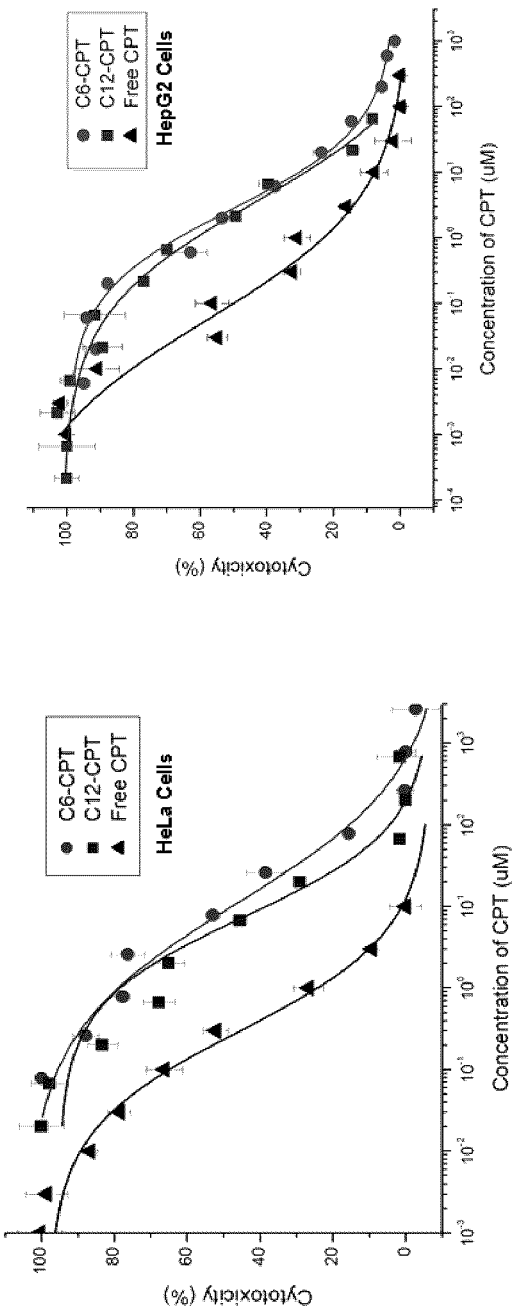
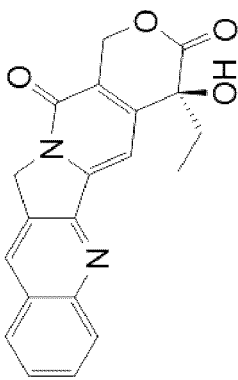
Figure 12

Reductive 6-O-Desilylations in CDs by DIBAL-H: Published Work

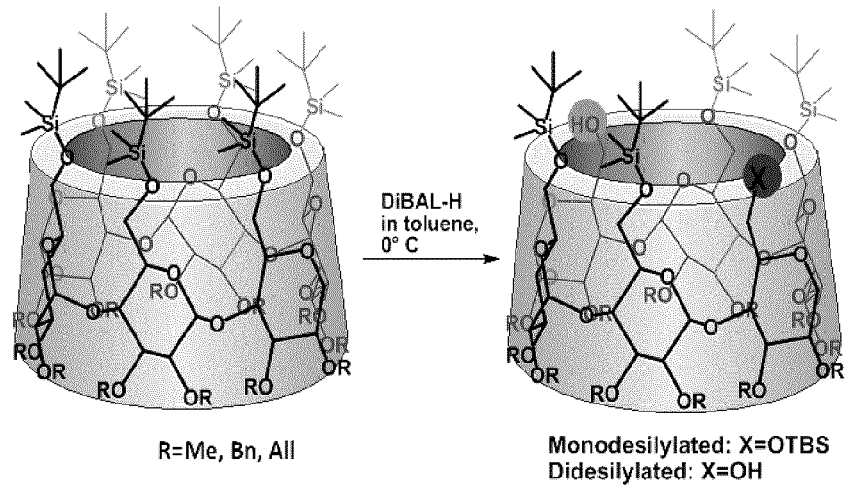

R=Me, Bn, All

Monodesilylated: X=OTBS
Didesilylated: X=OH

Unprecedented chemoselectivity: because of the mild conditions used, the following groups are not affected (in addition to Me)

- $PhCH_2$-, (Mono-ols); 70~87% ($6^A,6^D$-diols)
- All- 53~57% (Mono-ols); 60~63% ($6^A,6^D$-diols)

R. Ghosh, P. Zhang, A. Wang and C.-C. Ling, *Angew. Chem. Int. Ed.* 2012, 51, 1548.

Figure 13 – Prior Art

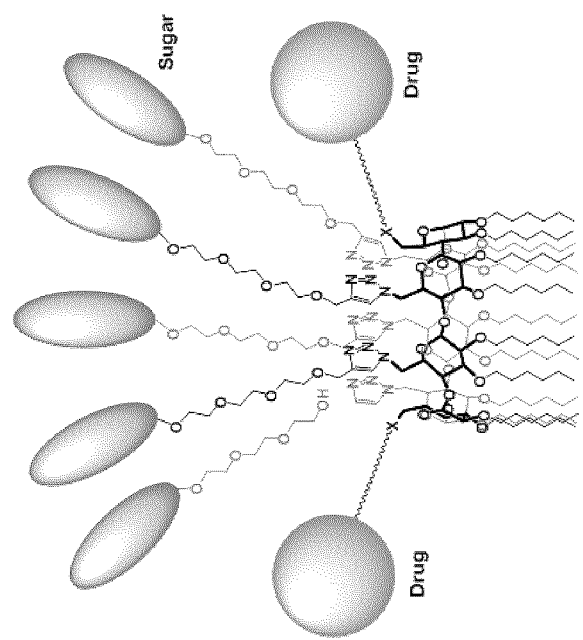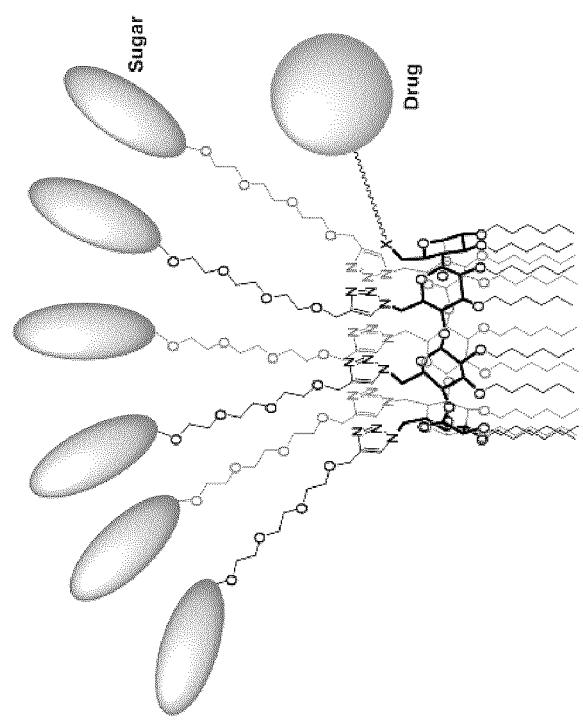
Figure 15

To assist the in vivo assays, other compounds were also prepared:
- A BSA-LacNAc conjugate containing ~36 LacNAc residues
- A LacNAc Monomer with similar linker
- A BSA-LNT conjugate was used as a comparison
- A cyclodextrin without LacNAc

TEM Images of Self-assembling Nanoparticles

WAX-III-145, 25-35 nm

Synthesis: Other Self-assembling Glycodendrimers

RAM-291 R=H, R'=OH, D-galactose
RAM-293 R=OH, R'=H, D-glucose
RAM-294 R=β-Gal(1->), R'=H, lactose ELISA ASSAY OF SHIGA-LIKE TOXIN STX1 USING MICROTITER PLATE
COATED WITH PK-TRISACCHARIDE-β-CD CONJUGATES COMPRISING
C6 AND C12 ALKYL GROUPS Binding of Stx1 to by $P^k$-cyclodextrins coated to microtiter plate ■ Stx1 binding to PZ5071
X50=55+/-3 ng/mL
● Stx1 binding to PZ5072
X50=45+/-1 ng/mL Stx1 concentration, ug/mL

Figure 28

AMPHIPHILIC CYCLODEXTRIN-BASED GLYCODENDRIMERS

The present application is the U.S. National Stage of International Patent Application No. PCT/CA2014/050944, filed Oct. 1, 2014, which claims the benefit of U.S. Provisional Application No. 61/885,151, filed Oct. 1, 2013, both of which are incorporated herein by reference.

FIELD

The present application pertains to the field of cyclodextrins. More particularly, the present application relates to amphiphilic cyclodextrin-based glycodendrimers.

BACKGROUND

Cyclodextrins (CDs) are a class of non-toxic, water-soluble D-glucose based macrocycles with a hydrophobic cavity. CDs typically vary by the number of glucose units. Common members include α-CD (6 glucose units), β-CD (7 glucose units) and γ-CD (8 glucose units), with increasing cavity size. The varying cavity sizes offer increased utility in a wide variety of applications, particularly in drug delivery models. For example, CDs can be used to form "inclusion complexes" in which a drug is included and carried within the cavity. This can be used as a pharmaceutical excipient to improve drug water solubility, chemical stability, and removal of certain drug side effects (such as undesirable taste). CDs have also drawn interest in the cosmetic and food additives industries, in the design of artificial enzymes, gene delivery vehicles, sensors and novel supramolecular assemblies.

CDs can be native or chemically modified on either or both of their primary and/or secondary faces. Typically, an inclusion complex has lower water solubility than native CDs. Chemical modifications of CDs can change their physico-chemical properties. For example, adding a tosyl group on the primary face of the β-CD renders the molecule near insoluble at room temperature, while adding methyl groups at OH-6 and OH-2 positions significantly increases water solubility. The toxicity of the molecule can also be changed. Therefore, modification of the CD molecule may present certain advantages. However, chemical modification of CDs is typically difficult to achieve, often leading to the formation of a mixture of products that are difficult to separate.

Amphiphilic CDs have generated considerable interest. These can be obtained through the modification of one face of a CD molecule with aliphatic chains. Amphiphilic CDs behave like surfactants, but are generally more stable. They can self-assemble in water to form large organized entities such as micelles, liposomes and lipid bilayers, which can be used to "trap" molecules either in the CD cavity or in the hydrophobic zone formed by the lipophilic tails or in both areas. The trapped molecules can be drugs, food additives and the like. This can enhance delivery of the molecules to the desired end point. In organic solvents, amphiphilic CDs can form inversed micelles and other self-assembled systems.

Amphiphilic CDs are usually poorly water soluble but are generally soluble in some organic solvents. However, it can be difficult to dissolve them into water, even through diffusion. They tend to form very large aggregates and are unstable, causing them to precipitate out over time. This makes them difficult to use for a variety of applications, particularly where water solubility is crucial. Further, the nature of the chemical synthesis is particularly difficult, generating lower than desired yields and contaminated with unacceptable side products. In all CD molecules, there exist three types of hydroxyl groups attached to the C6, C2 and C3 positions of the D-glucopyranosyl unit. It is relatively straightforward to chemoselectively differentiate one hydroxyl group from another, but it is much more challenging to regioselectively differentiate between hydroxyl groups of the same type because of their identical chemical properties.

Therefore, there is a need for water soluble amphiphilic CDs which are suitable for use in commercial applications.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide an amphiphilic cyclodextrin-based glycodendrimer. In accordance with one aspect, there is provided an amphiphilic cyclodextrin (CD)-based compound of the formula I:

R-G-D-A            (I)

wherein R is one or more hydrophilic groups; G is one or more linkers; D is a cyclodextrin, and
A is one or more aliphatic groups.

In certain embodiments, the amphiphilic cyclodextrin (CD)-based compound is:

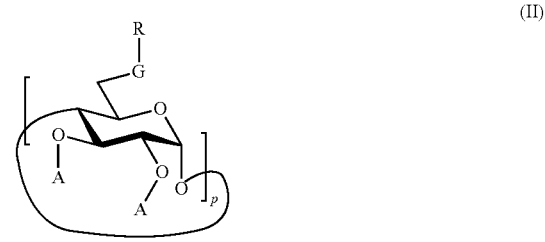

where R, G and A are defined herein and wherein the cyclodextrin subunit is shown where p is 6 to 8, typically 7.

In certain embodiments, R is a polar group, particularly a sugar moiety, G is a PEG group, and D is a cyclodextrin comprising 6, 7 or 8 dextrin subunits, particularly 7 subunits. G can be a PEG group of the formula $(CHR'CH_2O)_n$— where R' is H or $CH_3$ and n is 1 to 20, particularly n=4. G can also be any alkyl group substituted with the PEG group. G can further comprise a functional group, such as 1,2,3-triazole.

In certain embodiments, the sugar is lactose.

In certain embodiments, the one or more aliphatic groups in A are $C_3$ to $C_{18}$ alkyl groups, particularly $C_6$.

The amphiphilic CD-based glycodendrimer can be used for applications such as drug delivery, an additive in cosmetic, food formulations, a carrier (such as for a marker), ELISA, and the like, for example.

In another aspect, there is provided a method of drug delivery comprising administering the amphiphilic CD-based glycodendrimer as described herein, together with the drug, to a subject in need thereof.

In accordance with another aspect, there is provided a method of treating an infection by administering amphiphilic CD-based glycodendrimer as described herein, or a derivative thereof, wherein A is H or one or more aliphatic groups optionally substituted with a sugar moiety. Group A can also be any other suitable linker group bearing a sugar moiety.

The amphiphilic CD-based glycodendrimers as described herein have particular advantages, for example:

1. Water-solubility. In certain embodiments, the solubility of the compound can be further improved over described CD-based compounds either by the adjusting the length of the aliphatic group, the length of the PEG, or through chemical modification of the hydrophilic group.

2. Self-assembly in water to form nanoparticles of <100 nm sizes using the DMSO method. These sizes are particularly desirable for drug delivery as compared to nanoparticles which are >100 nm.

3. Stability. In certain embodiments, the present compounds form nanoparticles that are stable over a period of time. In one example, a water solution comprising a $C_6$ glycodendrimer stayed clear for more than two months without re-precipitation.

4. Nanocarriers. Form inclusions with organic molecules such as drugs (Camptothecin, CPT), dyes, etc., which enhance their water solubilities.

5. Enhance cellular uptakes of encapsulated compounds. These can be used for passive or active (by targeting lectins, for example) drug targeting.

6. Block bacterial adhesion. Potential to treat bacterial colonizations in intestines; remove toxins, autoantibodies.

7. As a tool in assaying, such as ELISA. Certain embodiments of the present compound with Pk-trisaccharides were found to coat the ELISA plates, and can be used for assaying toxins. These can be used, for example, to immobilize/separate bacteria cells and toxins and other biological receptors that recognize epitopes.

8. Low toxicity.

9. Synthesis can be scaled up.

BRIEF DESCRIPTION OF THE FIGURES

For a better understanding of the present invention, as well as other aspects and further features thereof, reference is made to the following description which is to be used in conjunction with the accompanying drawings, where:

FIG. 12 shows a study of the delivery of camptothecin to HeLa and HepG2 cells.

FIG. 13 shows a prior art synthesis of CDs comprising methyl, benzyl and allyl groups.

FIG. 15 illustrates the conjugation of a drug to the present compound.

FIG. 28 shows the results of an ELISA binding assay of Shiga-like toxin Stx1 to a microtiter plate coated with Pk-trisaccharide-β-CD conjugates comprising C6 and C12 alkyl groups.

DETAILED DESCRIPTION

Figure 1:
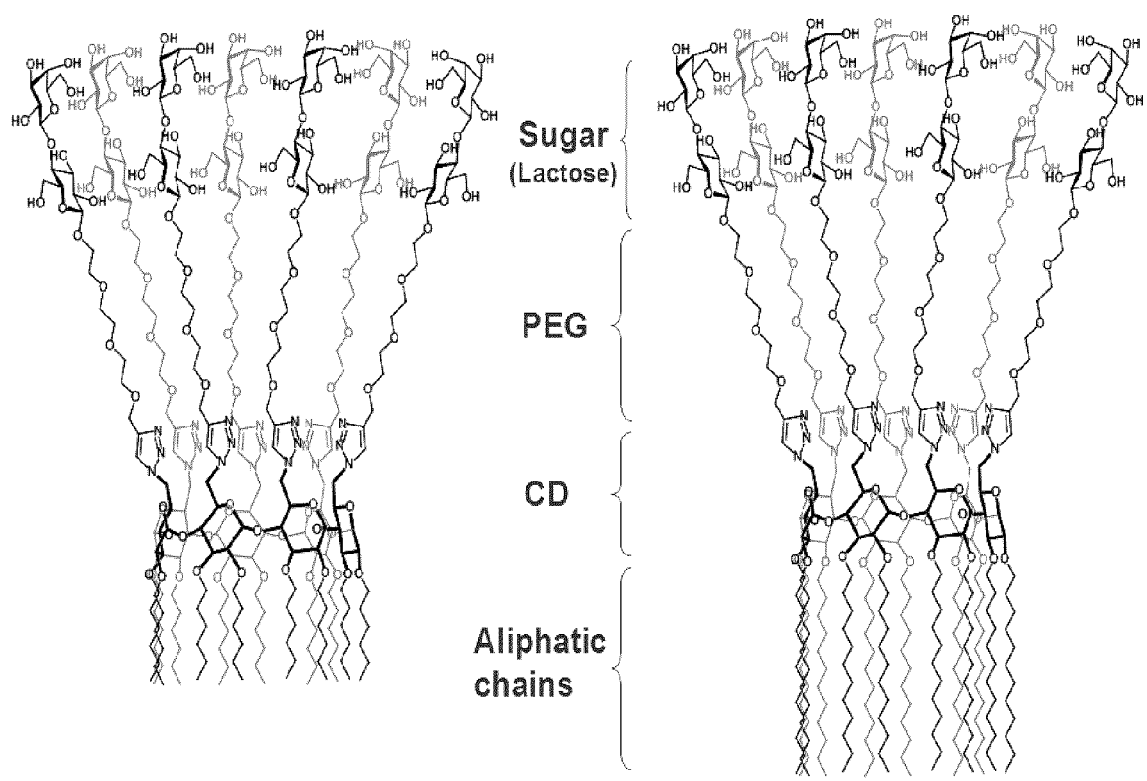
FIG. 1 shows two exemplary CD-based amphiphilic glycodendrimers in accordance with the present application.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, the term "aliphatic" refers to a linear, branched or cyclic, saturated or unsaturated non-aromatic hydrocarbon. Examples of aliphatic hydrocarbons include alkyl groups.

As used herein, the term "alkyl" refers to a linear, branched or cyclic, saturated or unsaturated hydrocarbon group which can be unsubstituted or is optionally substituted with one or more substituent. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups. The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

Chemical functional groups, such as ether, thioether, sulfoxide, sulfone, or amine, amide, ammonium, ester, phenyl, 1,2,3-triazole, and the like, can be incorporated into the alkyl group to help extend the length of the chain. For example, the linker group G can further comprise a 1,2,3-triazole group, together with the —(CHR'CH$_2$O)$_n$— group as defined herein.

As used herein, the term "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties.

As used herein, the term "hydrophilic" refers to the physical property of a molecule or chemical entity or substituent within a molecule that tends to be miscible with and/or dissolved by water, or selectively interacts with water molecules. Hydrophilic groups can include polar groups. By contrast, as used herein, the term "hydrophobic" refers to the physical property of a molecule or chemical entity or substituent within a molecule that tends to be immiscible with and/or insoluble in water, or selectively repels water molecules.

As used herein, the term "lipophilic" refers to the physical property of a molecule or chemical entity or substituent within a molecule that tends to be miscible with and/or dissolved by lipids, or selectively interacts with lipid molecules. A hydrophobic moiety may or may not be lipophilic, although these terms are not intended to be used synonymously unless explicitly stated.

As used herein, the term "amphiphilic" refers to the physical property of a molecule or chemical entity that possesses both hydrophilic and hydrophobic properties.

In the present document, the hydrophobic groups are illustrated to be placed at the secondary face of a CD while the hydrophilic groups are placed at the primary face of a CD. These two groups can be swapped to link to the opposite face of a CD.

As used herein, the term "sugar" refers to a carbohydrate ring structure, dimer, or polymer thereof comprising C, O and H and often of the general formula $C_m(H_2O)_n$ or modified forms such as aminosugars, acyclic forms of carbohydrates. Exemplary sugars are mono-, di-, tri- and poly-saccharides, such as, but not limited to, glucose, sucrose or lactose, for example. The linking position to the "sugar" is not limited to the anomeric center of the reducing end unit, but can be to any position of the sugar unit, and the linking functionality can be ether, thioether, sulfoxide, sulfone, amine, ammonium, amide, ester, phosphate or an aromatic group such as the pheny, 1,2,3-triazole group etc.

As used herein, the term "glycodendrimer" refers to a dendrimer comprising a sugar moiety. A "dendrimer" refers to any polymer or oligomer having branches of atoms strung off of a central spine.

The present application is directed to a class of novel cyclodextrin (CD)-based amphiphilic glycodendrimers. In certain embodiments, the glycodendrimer is a compound which comprises a CD core, hydrophilic groups bound thereto via polyethylene glycol (PEG) linkages, and a one or more aliphatic groups. Generally speaking, the compound has a hydrophilic portion and a hydrophobic aliphatic portion. The CD core comprises any number of glucose sub-units. In certain embodiments, there are 5, 6, or 7 glucose subunits, typically 7. Therefore, in certain embodiments, a β-CD is contemplated.

The CD can be substituted with any suitable hydrophilic group, including polar groups. One example is a sugar. Typically, the sugar is a disaccharide, such as lactose. However, it will be appreciated that other sugar groups may be used such as glucose, galactose, mannose, neuraminic acid, fructose, or the like. To help the water-solubility of the amphiphilic CD-based dendrimers, the sugar groups can be replaced with any other hydrophilic groups, including polar groups, such as amine and ammonium groups and their substituted variants, carboxylates, sulfonates, sulfates, phosphates and the like.

The hydrophilic moiety can be attached to the CD by a tether or linker. In certain embodiments, the hydrophilic group is a sugar which is tethered by a group comprising a PEG group. The PEG group typically has the formula —(CHR'CH$_2$O)$_n$—, where R' is H or CH$_3$, or is an alkyl group substituted with —(CHR'CH$_2$O)$_n$—. The PEG can be any length available from commercial sources, but is typically where n is 1-20, more particularly n=4, and wherein R'=H. The length of PEG is found to be ideal to produce a cost-effective water soluble compound. Typically, with a PEG length of 4, the water solubility of the compound remains ideal; adjustments can be made to the lengths of the aliphatic groups tethered to the CD moiety. Short PEG chains can also be joint together via chemical functionalities such as amine, ammonium, amide, thioether, sulfoxide, sulfone, 1,2,3-triazole and others.

The CD typically comprises a primary face (comprising the hydrophilic groups) and a secondary face. On the secondary face of the CD are attached one or more, typically a plurality of aliphatic chains. In certain embodiments, the chains are bonded to either O2 or O3, or both O2 and O3 groups. The length of the aliphatic chain can vary from $C_1$-$C_{20}$, typically $C_3$-$C_{18}$, but is typically $C_6$, $C_8$ or $C_{12}$. In particular embodiments, the length is $C_6$.

FIG. 1 shows two exemplary compounds in accordance with the present application. Both structures are based on the general formula

R-G-D-A    (I)

where R represents one or more hydrophilic groups, G represents one or more linkers, D represents a cyclodextrin and A represents one or more aliphatic groups. In these exemplary compounds, R is lactose, while G comprises —$(CH_2CH_2O)_n$—, where n=4, and the number of D-glucose subunits is 7 (β). In the left panel, a plurality of $C_6$ groups are attached to the CD, while in the right panel, a plurality of $C_{12}$ groups are attached.

Thus, the cyclodextrin (CD)-based amphiphilic glycodendrimers as described herein are of the general structure:

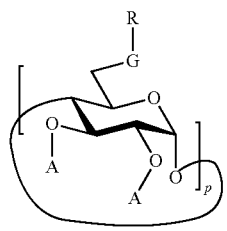

(II)

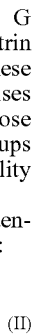

where R, G and A are described above, and the cyclodextrin subunit of D is shown, where p is 6 to 8, typically 7.

Figure 2:
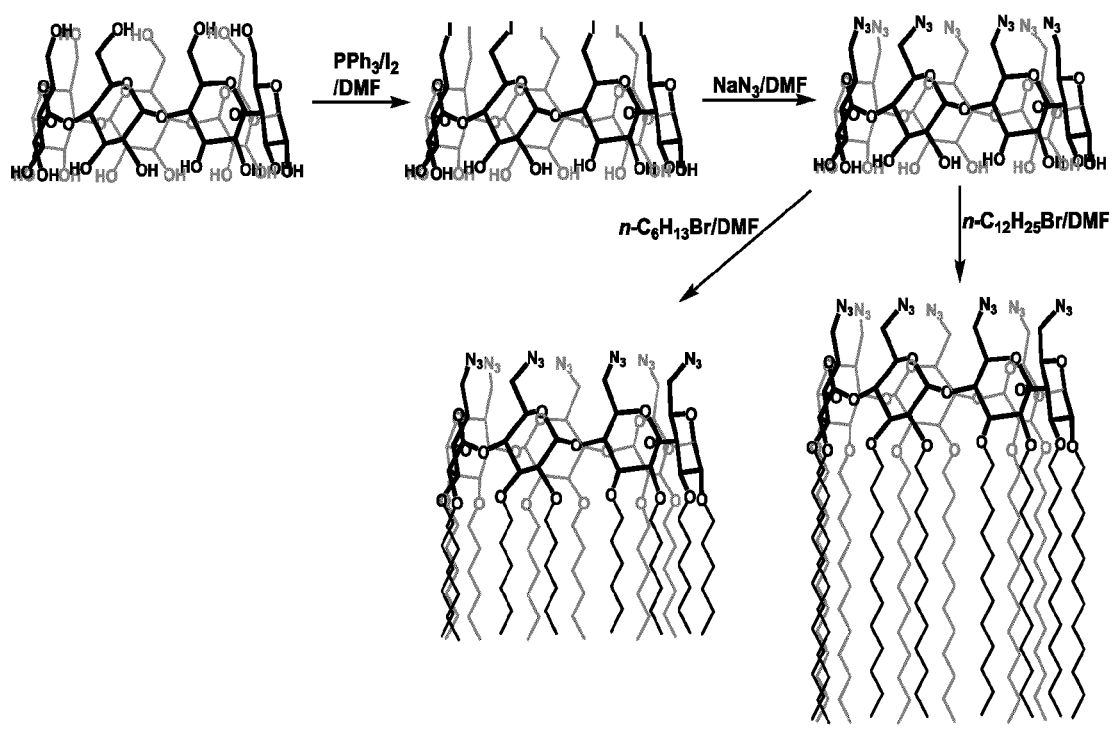
FIG. 2 shows an exemplary prior art synthesis for the attachment of $C_6$ and $C_{12}$ aliphatic chains to the CD.

FIG. 2 shows an exemplary synthesis for the attachment of $C_6$ and $C_{12}$ aliphatic chains to the CD according to known literature.

Figure 3:
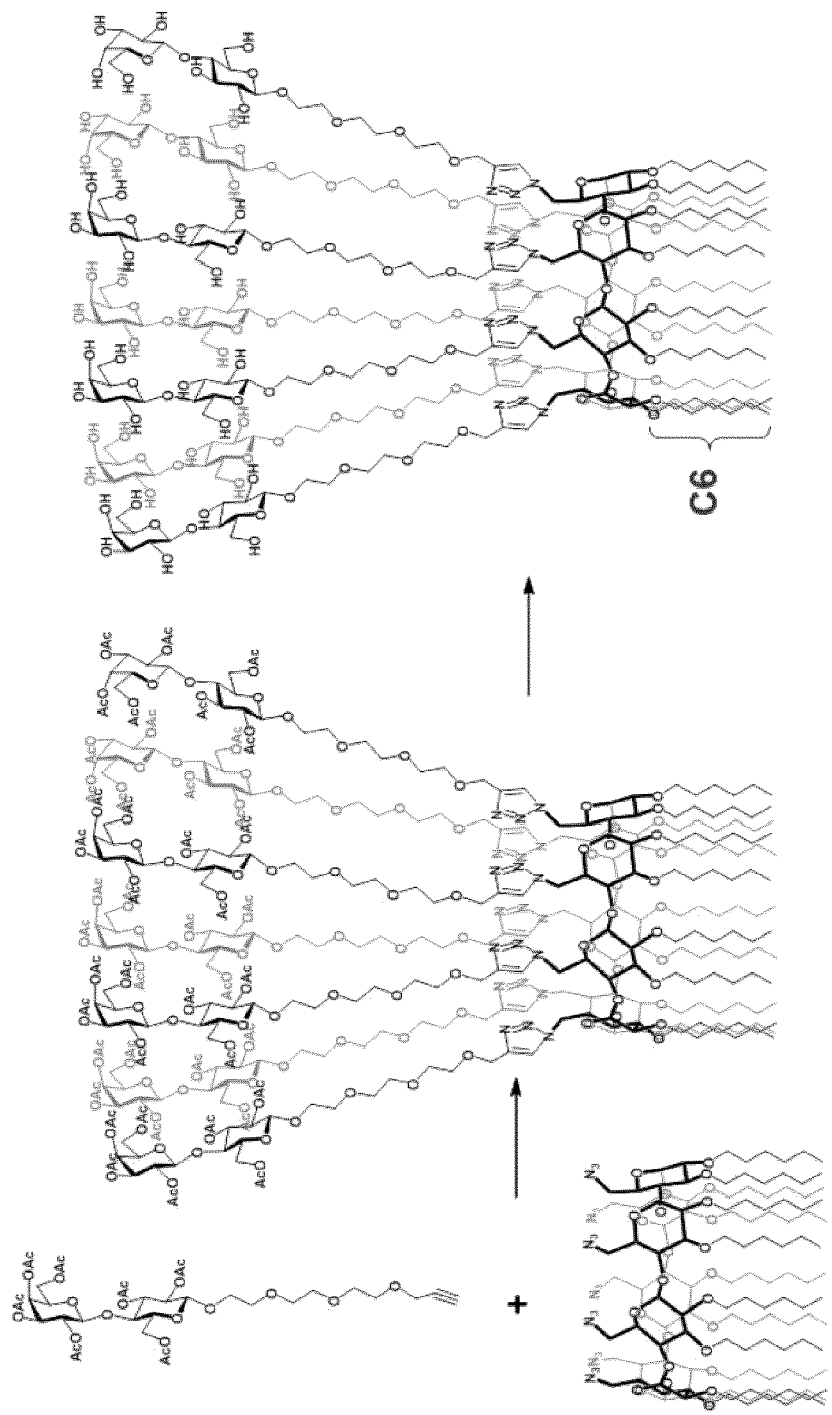
FIG. 3 shows an exemplary synthesis for the attachment of PEG-ylated lactose residues to a CD having $C_6$ aliphatic groups bound thereto.

FIG. 3 shows an exemplary synthesis for the attachment of PEG-ylated lactose residues to a CD having $C_6$ aliphatic groups bound thereto. Using lactose as a model, different glycodendrimers were synthesized using copper-mediated "click" chemistry. As would be understood, different hydrophilic groups, including different sugars, can be used in place of lactose.

Figure 4:
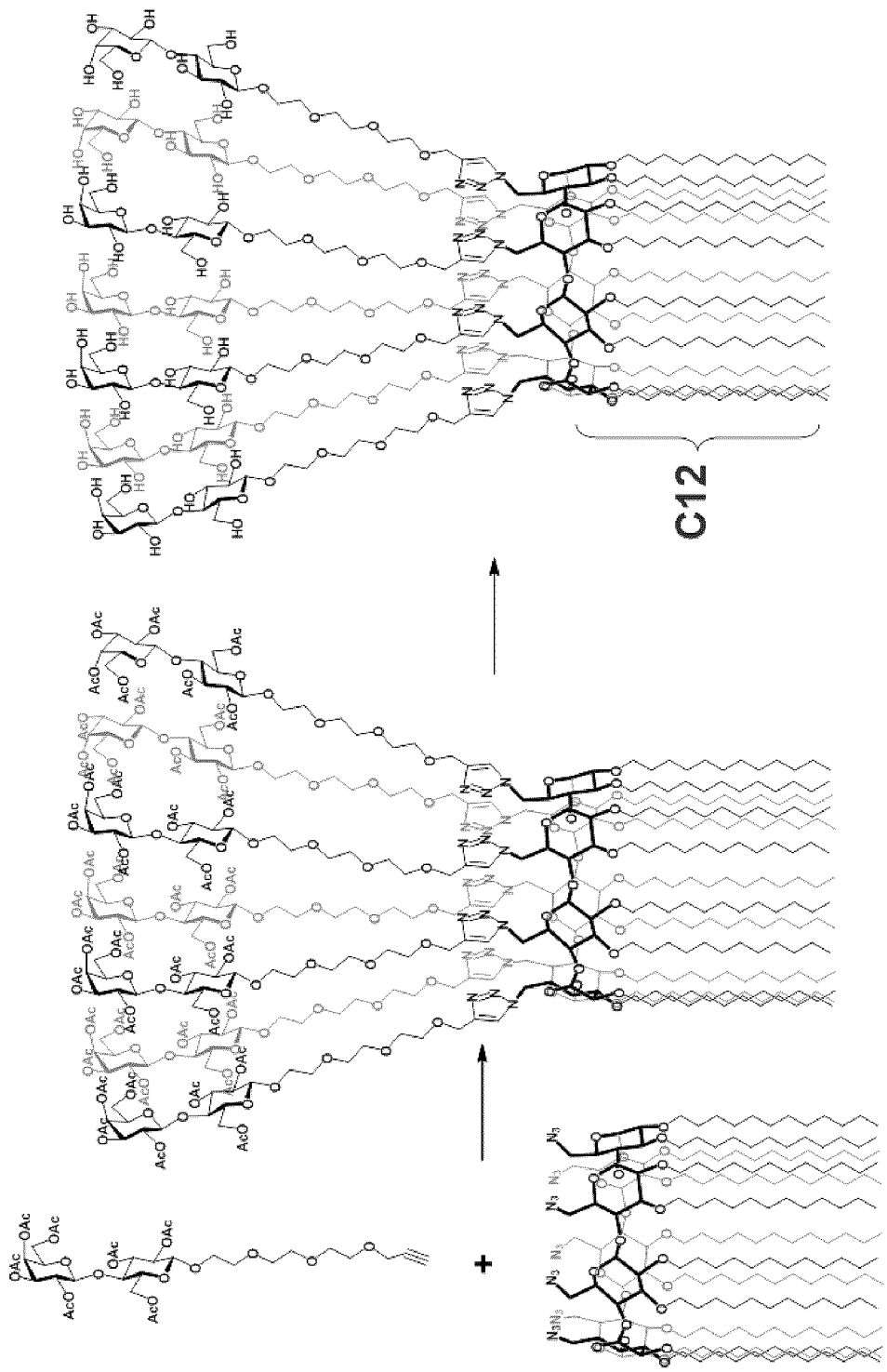
FIG. 4 is another example of the synthesis of FIG. 3, but with $C_{12}$ aliphatic groups on the CD.

FIG. 4 is another example of the synthesis of FIG. 3, but with $C_{12}$ aliphatic groups on the CD.

To gain a better understanding of the invention described herein, the following examples are set forth. It should be understood that these examples are for illustrative purposes only. Therefore, they should not limit the scope of this invention in any way.

EXAMPLES

Example 1: Water Solubility

Figure 5:
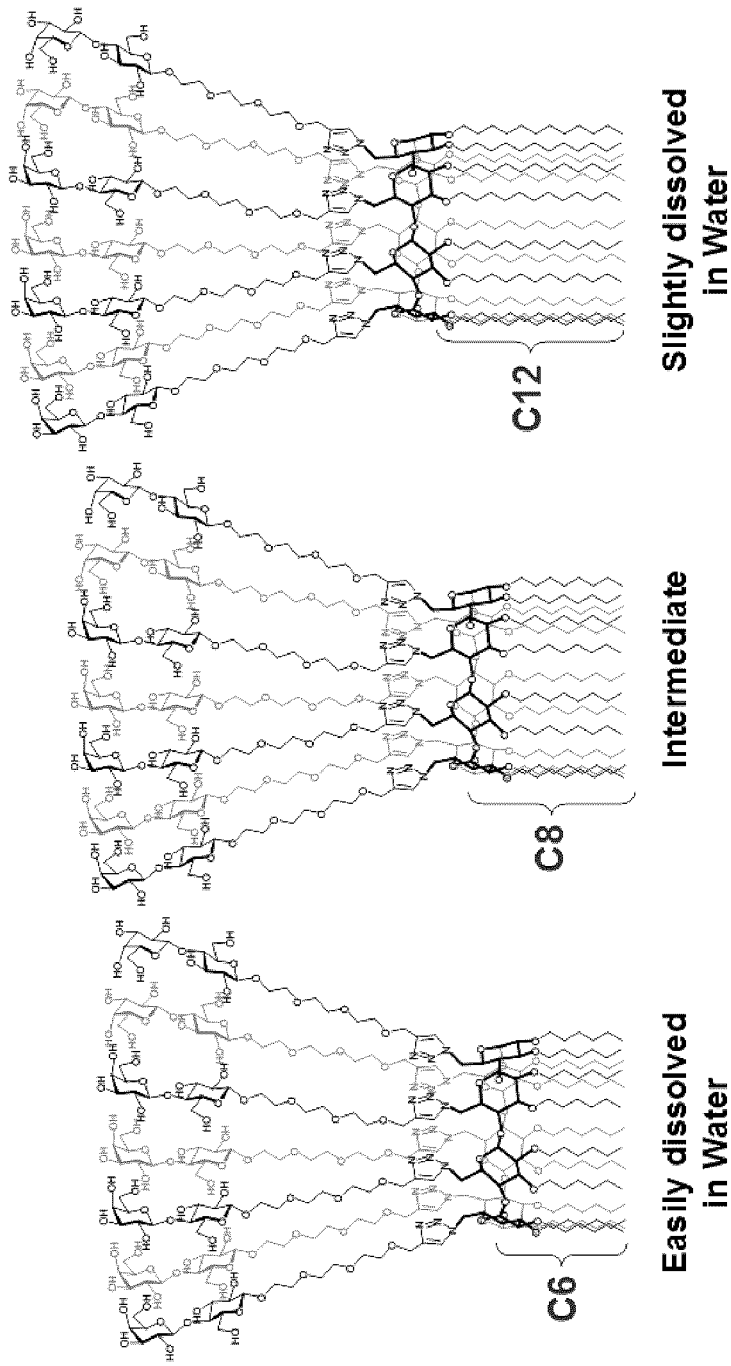
FIG. 5 shows relative solubility of the present CD compounds in water.

CD-based glycodendrimers comprising lactose residues and four PEG residues were compared for solubility in water. As shown in FIG. 5, glycodendrimers comprising $C_6$ aliphatic groups easily dissolved in water, while $C_8$ aliphatic groups possessed intermediate solubility. The glycodendrimer comprising $C_{12}$ aliphatic groups only slightly dissolved in water. Further, it was found that the $C_6$ version can be easily freeze-dried in solid form and is easier to handle for future use. It has also been found that mixing the present compound in DMSO with water will result the compound to self-assemble into micelles or other forms of aggregates. If a drug or other organic compounds are present in DMSO solution, after mixture the solution with water, the drug or organic compounds will be incorporated into the micelles as well as other forms of aggregates. The DMSO can then be readily removed by dialysis.

Figure 6:
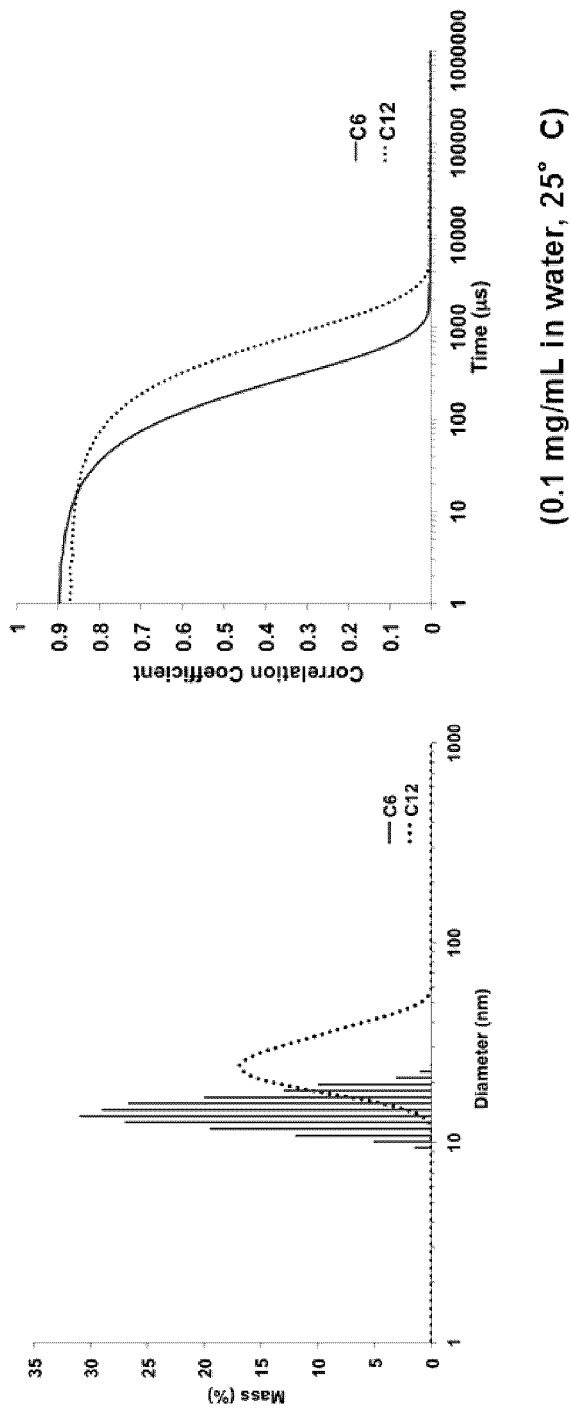
FIGS. 6 and 7 show dynamic light scattering spectra of lactose-CD conjugates comprising $C_6$ and $C_{12}$ aliphatic groups as well as their micelles formed with camptothecin and Nile Red
Figure 7:
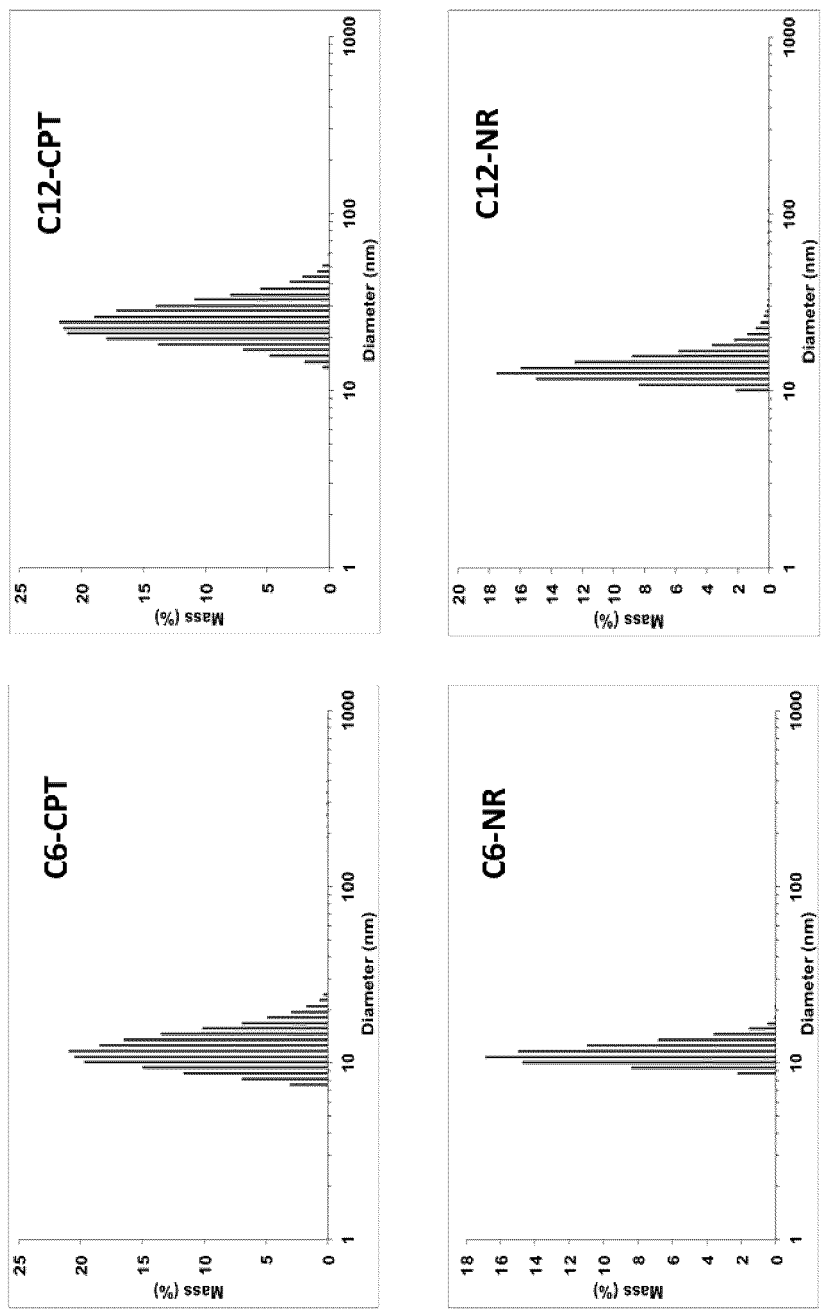

Example 2: Physico-Chemical Properties of Lactose-CD Conjugates Comprising $C_6$ Aliphatic Groups FIG. 6 shows dynamic light scattering spectra of lactose-CD conjugates comprising $C_6$ and $C_{12}$ aliphatic groups, and FIG. 7 shows dynamic light scattering spectra of each of the two conjugates with camptothecin and Nile Red dye.

Figure 8:
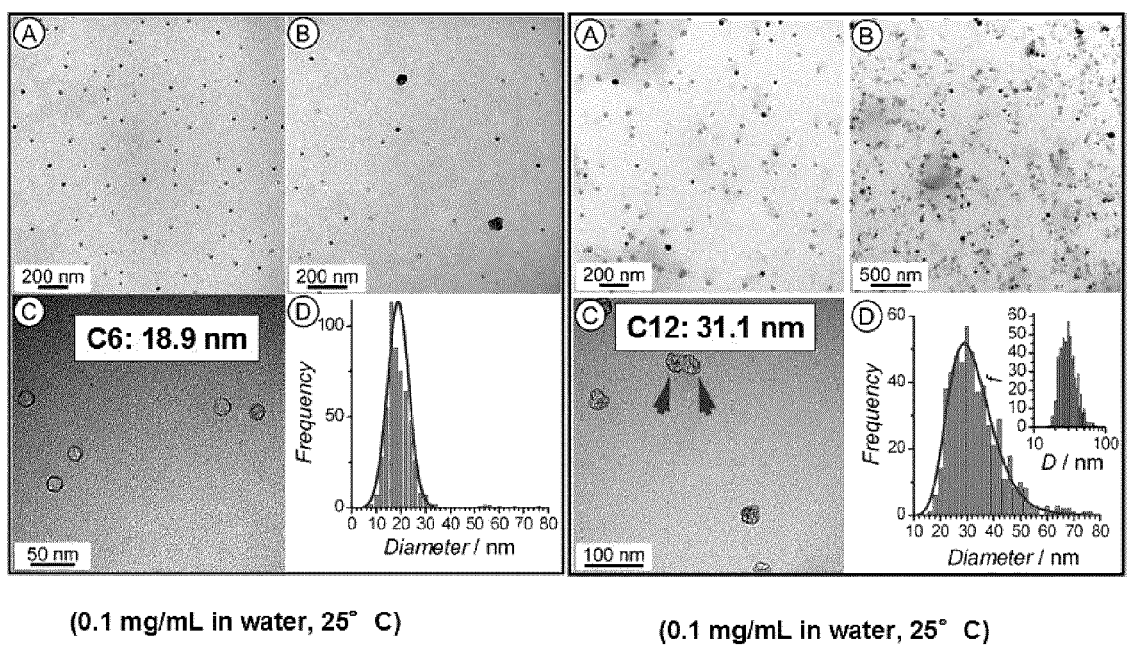
FIG. 8 shows transmission electron microscope images of two lactose-CD conjugates comprising both $C_6$ and $C_{12}$ aliphatic groups.

FIG. 8 shows transmission electron microscope images of the lactose-CD conjugates comprising $C_6$ and $C_{12}$ aliphatic groups.

Figure 9:
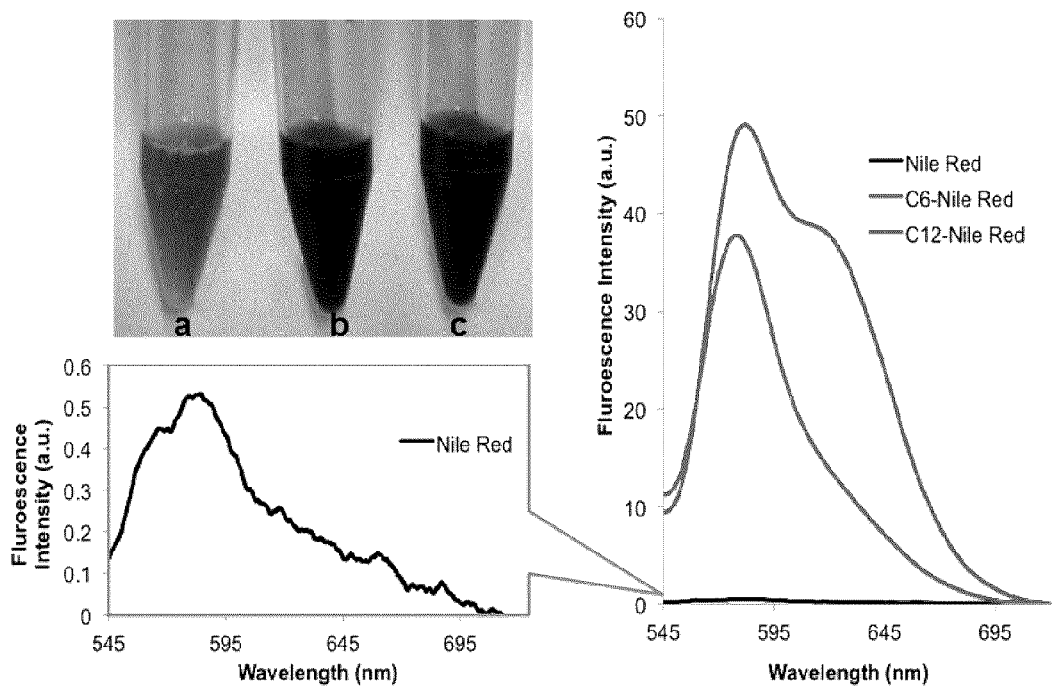
FIG. 9 shows the results of solubilisation of Nile Red dye in water as well as its enhanced solubilisation in water with the help of $C_6$ and $C_{12}$ Lactose-CD conjugates; the fluorescence spectra of the above three solutions.

FIG. 9 shows the results of inclusion of Nile Red dye into CD conjugates. The results indicate robust uptake of Nile Red in conjugates comprising $C_6$ and $C_{12}$ aliphatic groups. The results also show evidence of enhanced solubilisation of dye in the presence of both lactose-CD conjugates comprising $C_6$ and $C_{12}$ aliphatic groups.

Example 3: Cellular Uptake Studies with Dyes Using HeLa Cells

Figure 10:
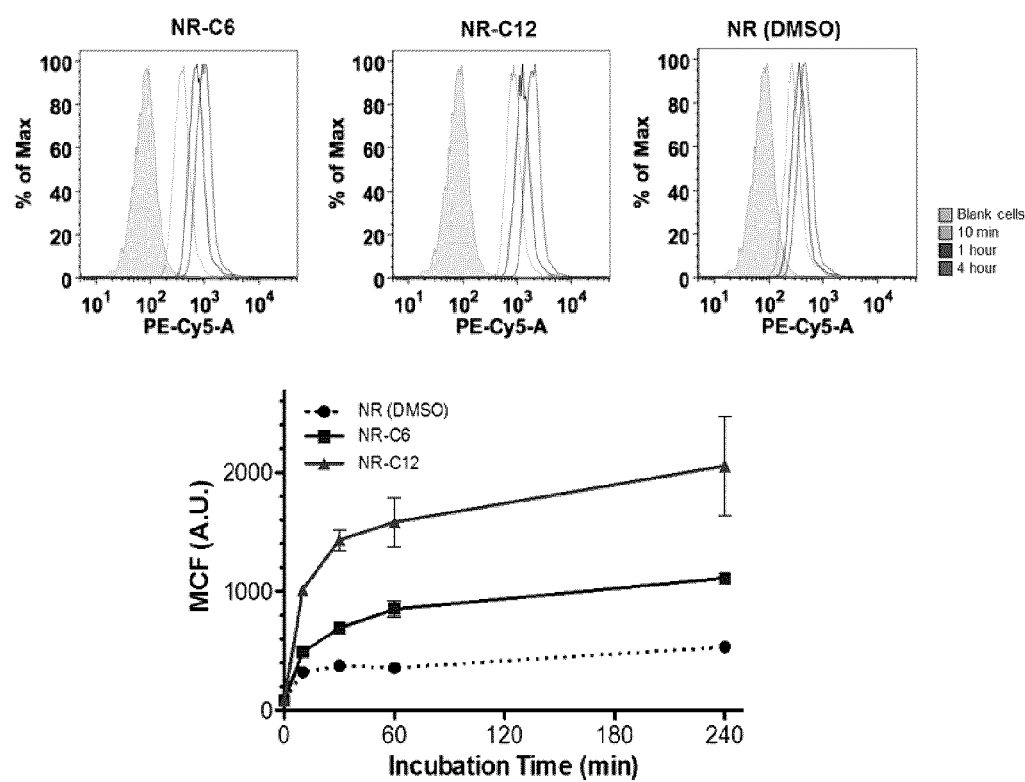
FIG. 10 shows results obtained from flow cytometry to compare the assisted cellular uptake of nile red in HeLa cells by $C_6$ and $C_{12}$ lactose-CD conjugates.
Figure 11:
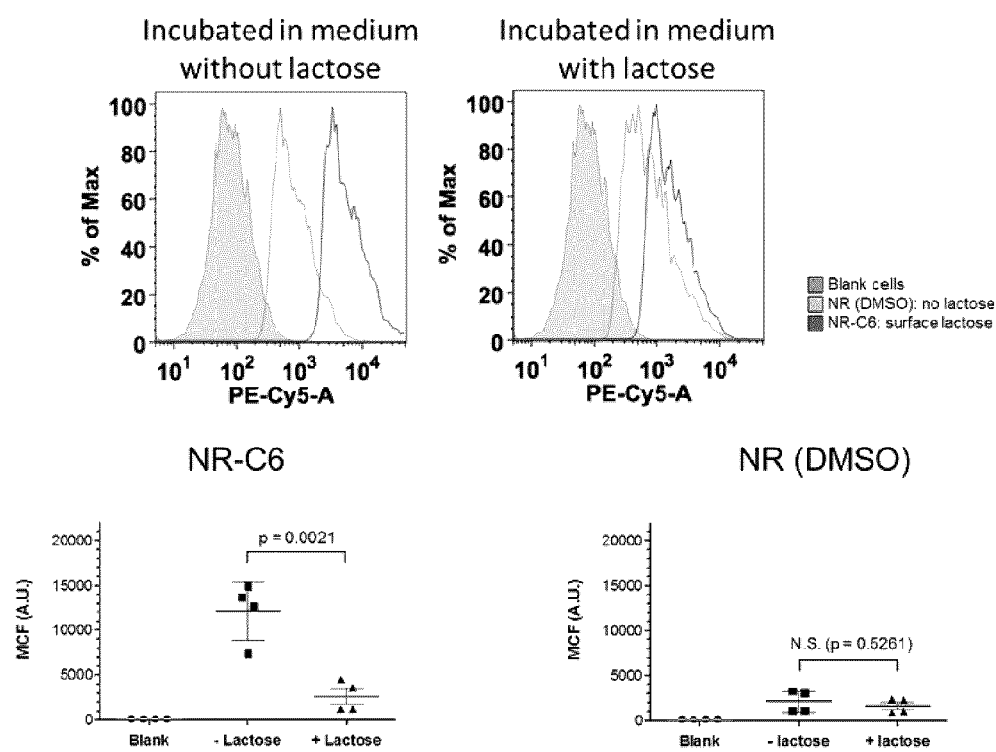
FIG. 11 shows the results from an inhibition experiment which confirms the cellular uptake of $C_6$ Lactose-CD conjugate is reduced by the presence of free lactose in the cell culture media.

FIG. 10 shows comparative cellular uptake of Nile red in HeLa cells by flow cytometry experiments. A steady increase of cellular uptake of Nile red was observed over a period of 4 hours. $C_{12}$ Lactose-CD conjugate was found to be better than the $C_6$ Lactose-CD conjugate. FIG. 11 shows the results from an inhibition experiment using HepG2 cells which express receptor than can bind lactose. Using the $C_6$ Lactose-CD conjugate as a career for Nile red, it was observed that the cellular uptake of the dye was inhibited with the presence of free lactose in the cell culture media.

Example 4: Cancer Cell Viability Assays

In these examples, both HeLa and HepG2 cells were subjected to delivery of camptothecin (CPT), which is highly toxic but water insoluble. The CPT was entrapped into the micelles formed by a lactose-CD conjugate comprising either $C_6$ or $C_{12}$ aliphatic groups. The results in FIG. 12 show that lactose-CD micelles can readily deliver CPT into both HeLa and HepG2 cells, illustrating the viability of lactose-CD conjugates as vessels for drug delivery, including water-insoluble drugs.

Example 5: Preparation of Conjugated CDs—Novel Chemistry

Previously, work done by Ghosh et al., *Angew. Chem. Int. Ed.* (2012) 51, 1548-52, illustrated reductive 6-O-desilylation in CDs using diisobutylaluminum hydride (DIBAL-H) (see FIG. 13). The results showed that DIBAL-H is an excellent reagent that can be used to promote regioselective O-desilylations of primary silyl ethers on CD derivatives. The method allows for the preparation of orthogonally protected, multi-substituted CD derivatives in an efficient manner. Compared to other known O-debenzylations, the O-desilylation requires easily accessible starting materials but a much smaller amount of reagent, and the reaction can be carried out under mild reaction conditions (Ghosh et al., supra).

Figure 14:
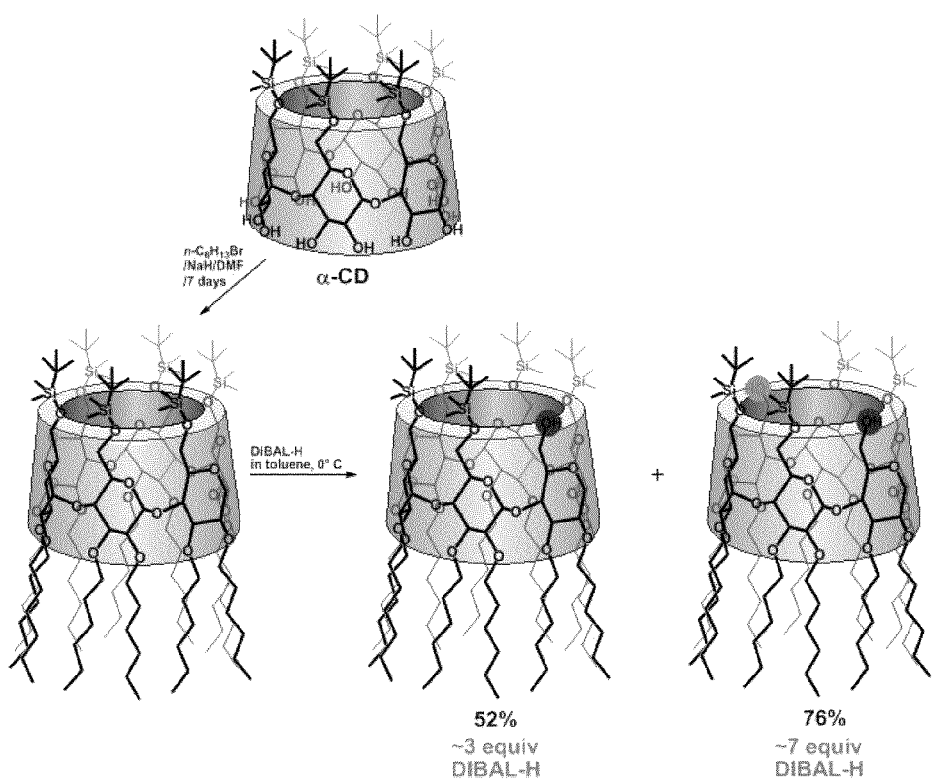
FIG. 14 shows a novel synthesis based on FIG. 13 using C6 aliphatic chain-functionalized α-CD derivative.

In the present application, the method was applied to prepare multifunctionalized amphiphilic CD dendrimers. As shown in FIG. 14, CDs comprising $C_6$ aliphatic groups were synthesized. FIG. 15 illustrates that these molecules could be further conjugated to form CDs with chemical functionalities for linking drug molecules via covalent linkages, while still maintaining the ability to deliver the same or other drug molecules in the formed nanoparticles.

Example 6: Targeting Bacterial Fimbrial Lectins

Figure 16:
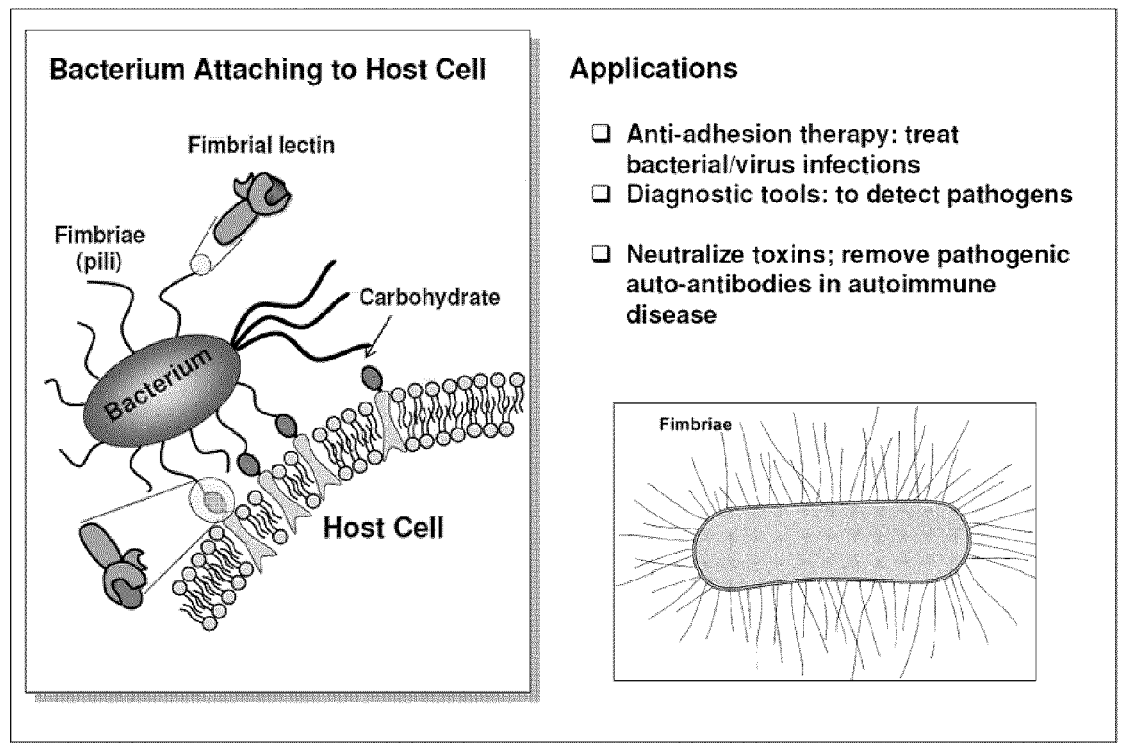
FIG. 16 illustrates a bacterium attaching to a host cell.
Figure 17:
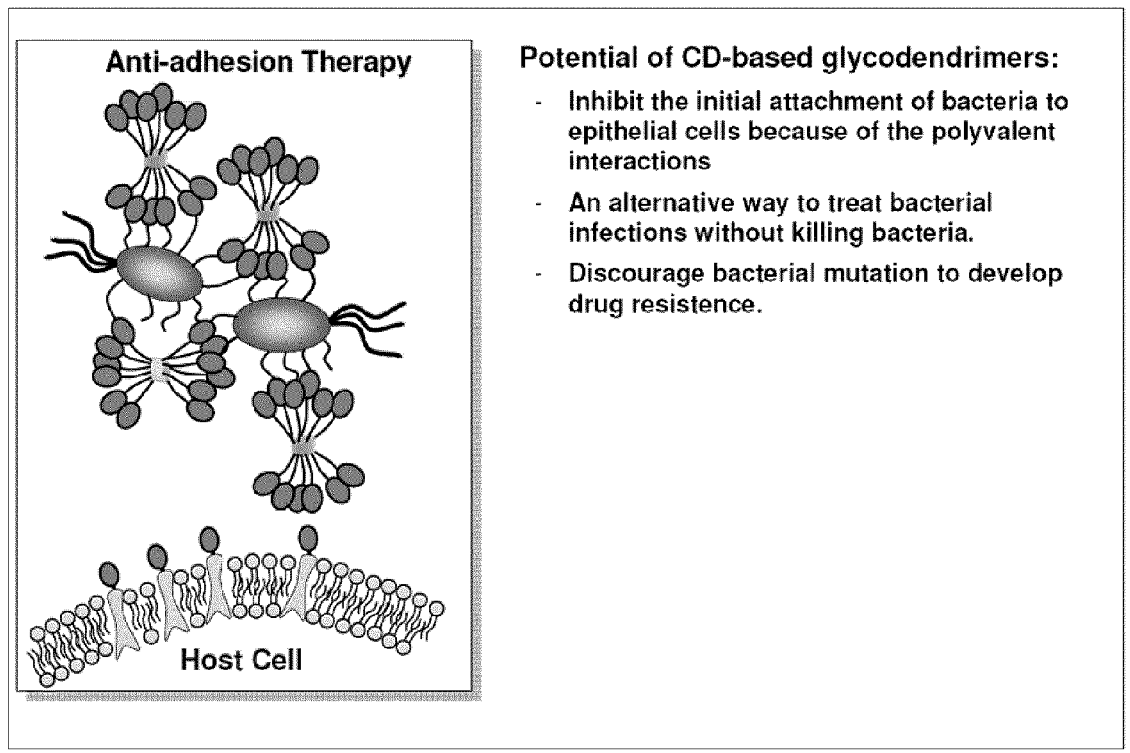
FIG. 17 illustrates a potential CD-based anti-adhesion therapy.

Bacteria attach to host cells using fimbriae which recognize carbohydrates on the surface of the host cell. It is contemplated that the compound as described herein could be used to target the bacterial fimbriae in anti-adhesion therapy to treat bacterial infections by inhibiting the initial attachment of bacteria to host cells, for example. The compound may also be used as a diagnostic tool to detect pathogens, immobilize pathogens, or to neutralize toxins, or to remove pathogenic auto-antibodies in autoimmune diseases, for example. See FIGS. 16 and 17.

Figure 18:
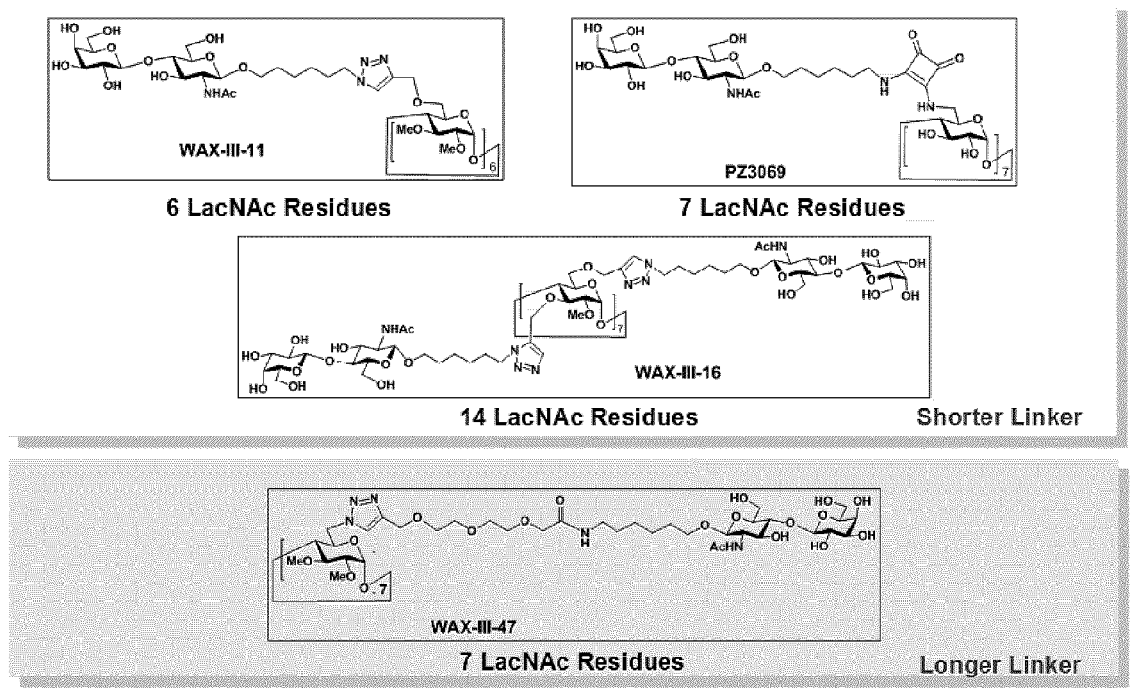
FIG. 18 shows several versions of CD-conjugated glycodendrimers containing N-acetyllactosamine (LacNAc) residues.

As one example, enteropathogenic *Escherichia coli* (EPEC) E2348/69 is known to recognize N-acetyllactosamine (LacNAc). Several versions of amphiphilic CD-based glycodendrimers containing LacNAc residues have been synthesized and are illustrated in FIG. 18.

Figure 19:
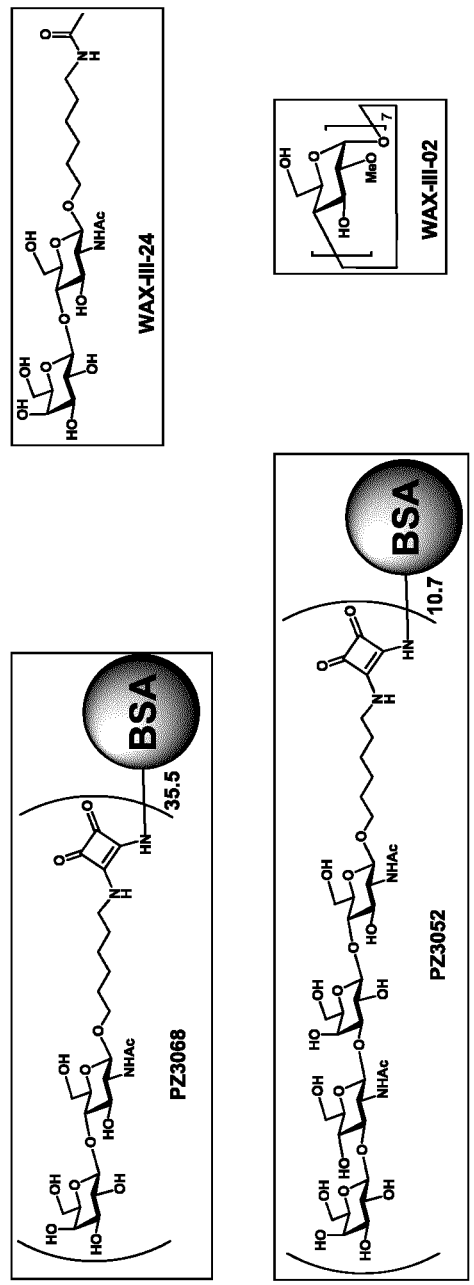
FIG. 19 shows examples of additional conjugates tested.

FIG. 19 shows additional examples of glycoconjugates synthesized. These glycodendrimers can be used to inhibit the localized adherence (LA) of EPEC E2348/69 to HEp-2 cells.

Figure 20:
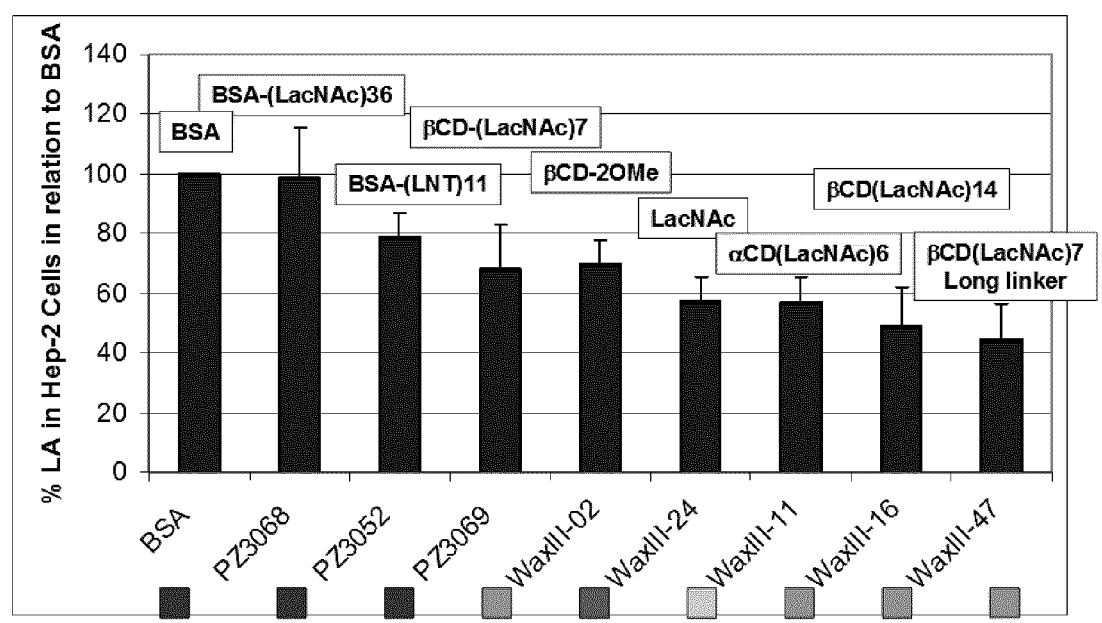
FIG. 20 shows a comparison of inhibition results using synthesized glycodendrimers to prevent localized adherence (LA) of enteropathogenic *Escherichia coli* (EPEC) E2348/69 to HEp-2 cells.

As shown in FIG. 20, all CD-based glycodendrimers are better inhibitors than BSA-based glycoconjugates. The length of the linker may be crucial in determining the degree of inhibition.

Figure 21:
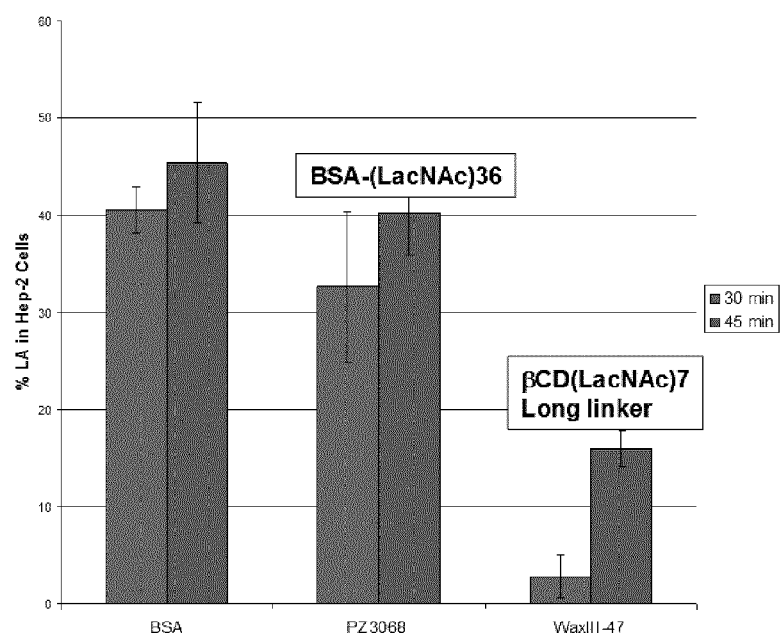
FIG. 21 shows the results of time-dependent LA inhibition in Hep-2 cells.

FIG. 21 shows the results of time-dependent LA inhibition assays using the EPEC E2348/69/HEp-2 cell system. Compound Wax-III-47 shows >95% inhibition when incubation time was 30 minutes, indicating that the localized adherence by bundle-forming pilus of EPEC E2348/69 were blocked by CD-based glycodendrimers.

Figure 22:
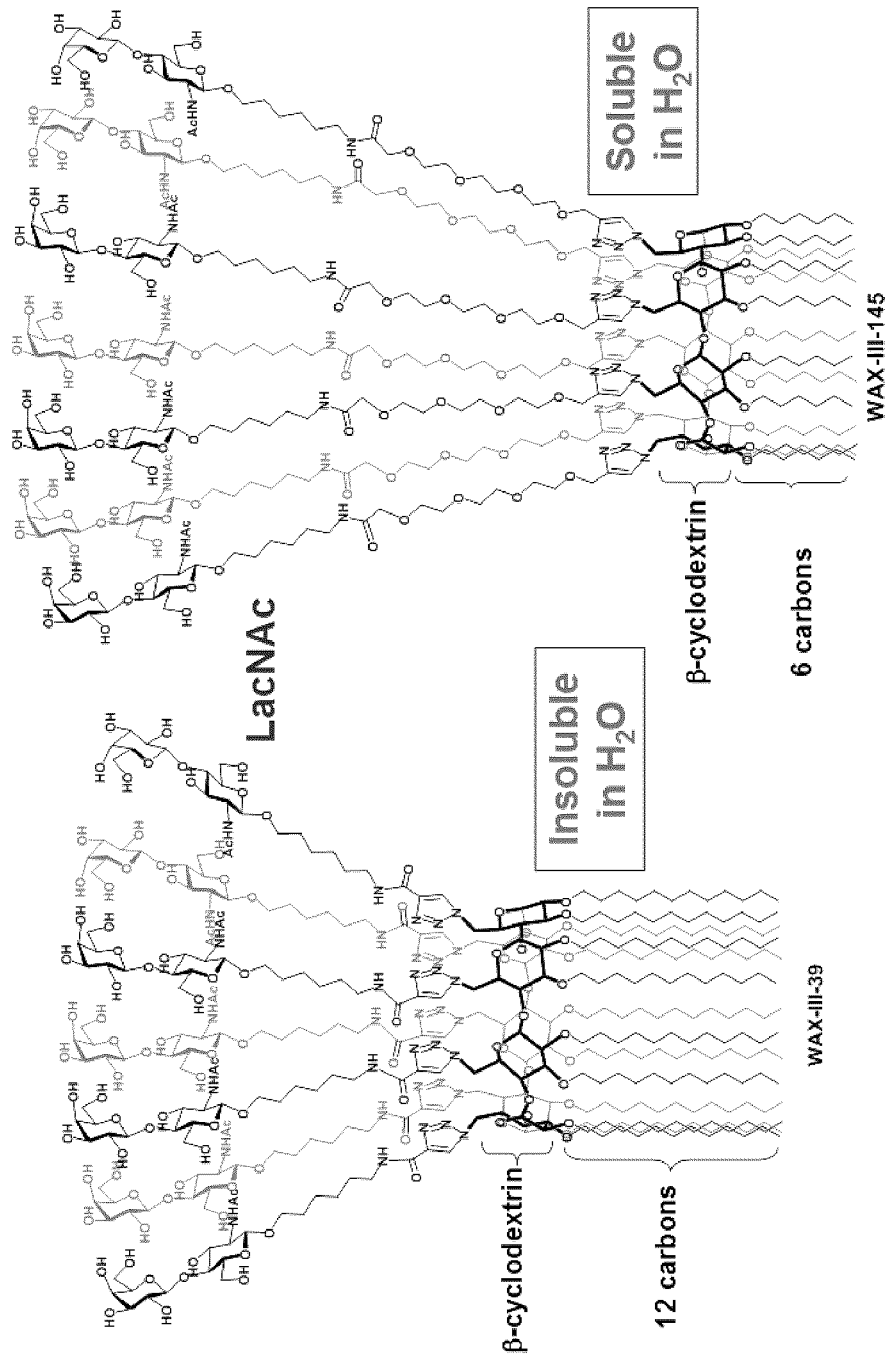
FIG. 22 shows two examples, WAX-III-39 and WAX-III-145 comprising LacNAc conjugated to β-CD and comprising $C_{12}$ and $C_6$ aliphatic groups, respectively.
Figure 23:
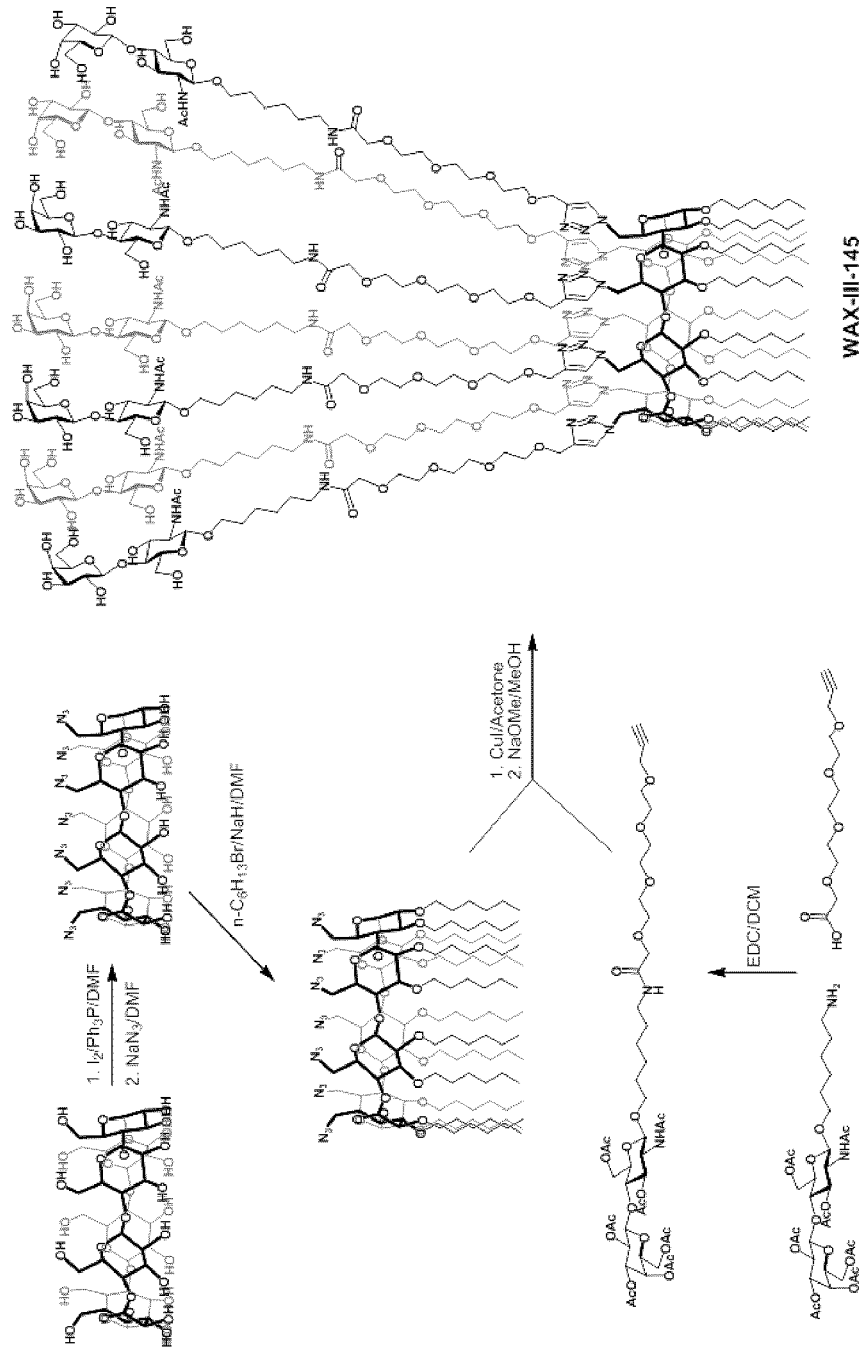
FIG. 23 shows an exemplary synthesis of a LacNAc-based self-assembling dendrimer (WAX-III-145).
Figure 24:
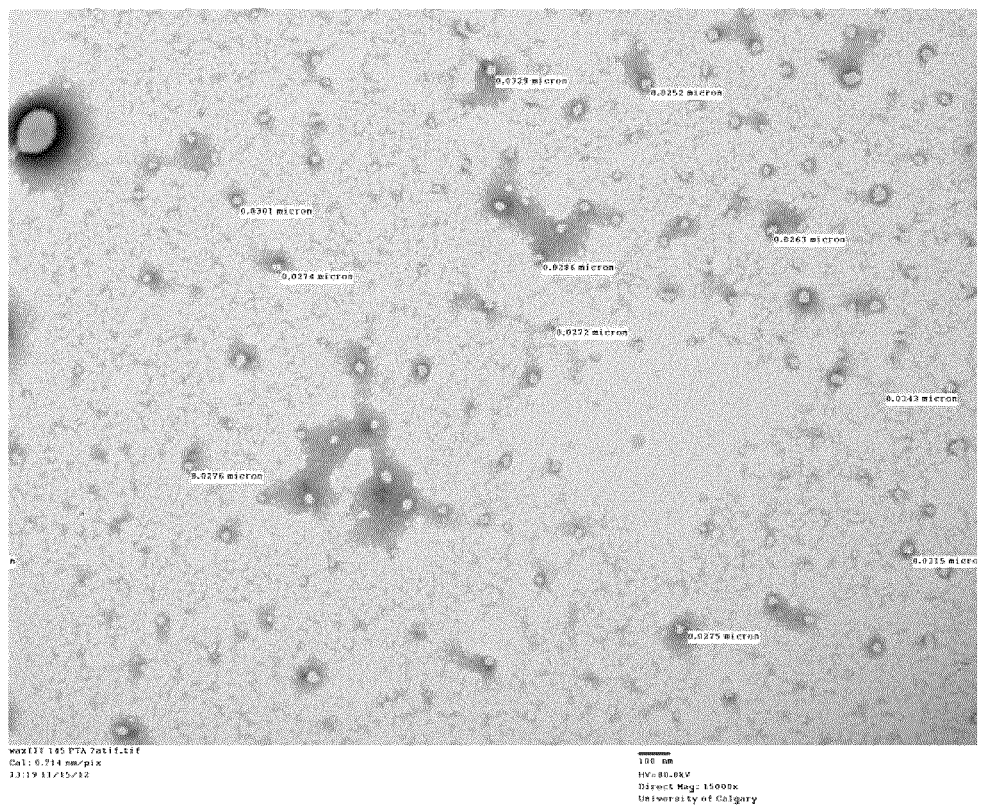
FIG. 24 shows transmission electron microscope images of the self-assembling WAX-III-145 dendrimers.

FIG. 22 shows two examples, WAX-III-39 and WAX-III-145 which are amphiphilic CD-conjugates comprising LacNAc residues and $C_{12}$ and $C_6$ aliphatic groups, respectively. FIG. 23 shows an exemplary synthesis of a LacNAc-based self-assembling dendrimer (WAX-III-145). FIG. 24 shows transmission electron microscope images of the self-assembling WAX-III-145 dendrimers.

Figure 25:
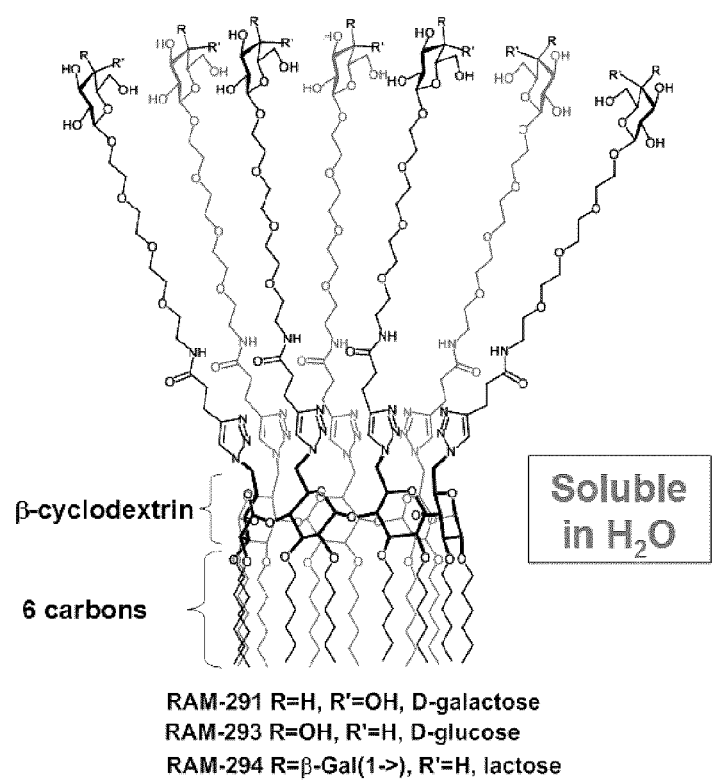
FIG. 25 shows examples of other self-assembling glycodendrimers.

Other synthesized self-assembling glycodendrimers are illustrated in FIG. 25.

Figure 26:
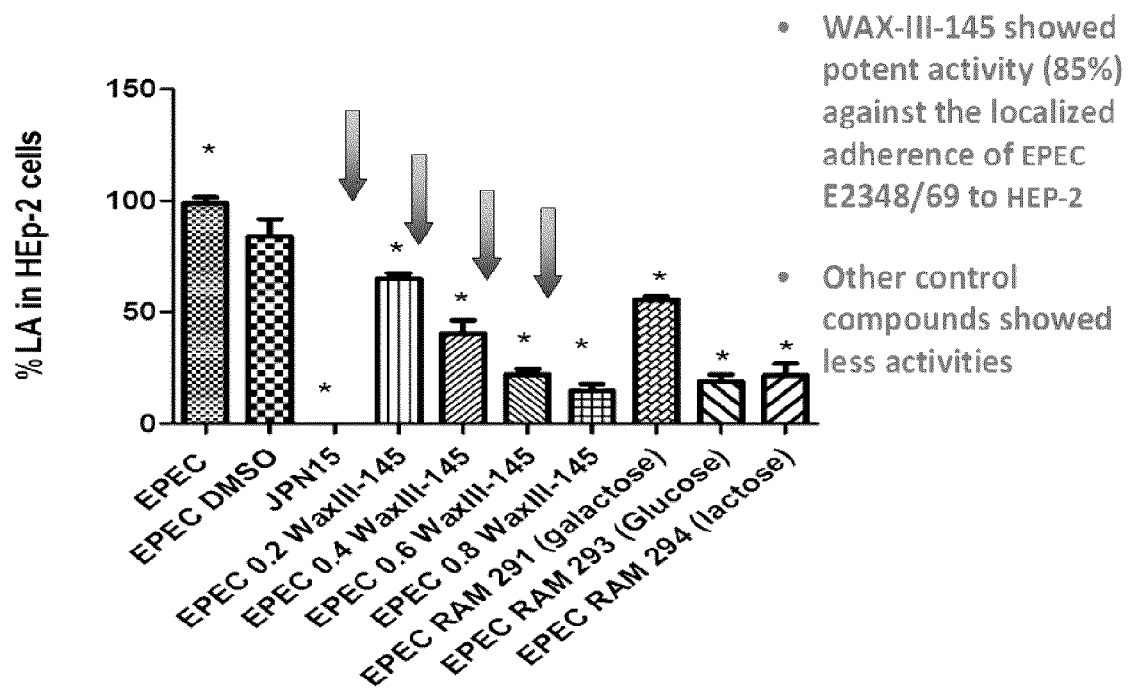
FIG. 26 shows results of an assay of inhibiting bundle forming pilus of EPEC E2348/69 using CD-based glycodendrimers.

FIG. 26 shows results of an assay of inhibiting localized adherence of bundle forming pilus of EPEC E2348/69 using CD-based glycodendrimers. The nanoparticles formed by amphiphilic WAX-III-145 showed potent activity (85%) against the localized adherence of EPEC E2348/69 to HEp-2 cells.

Figure 27:
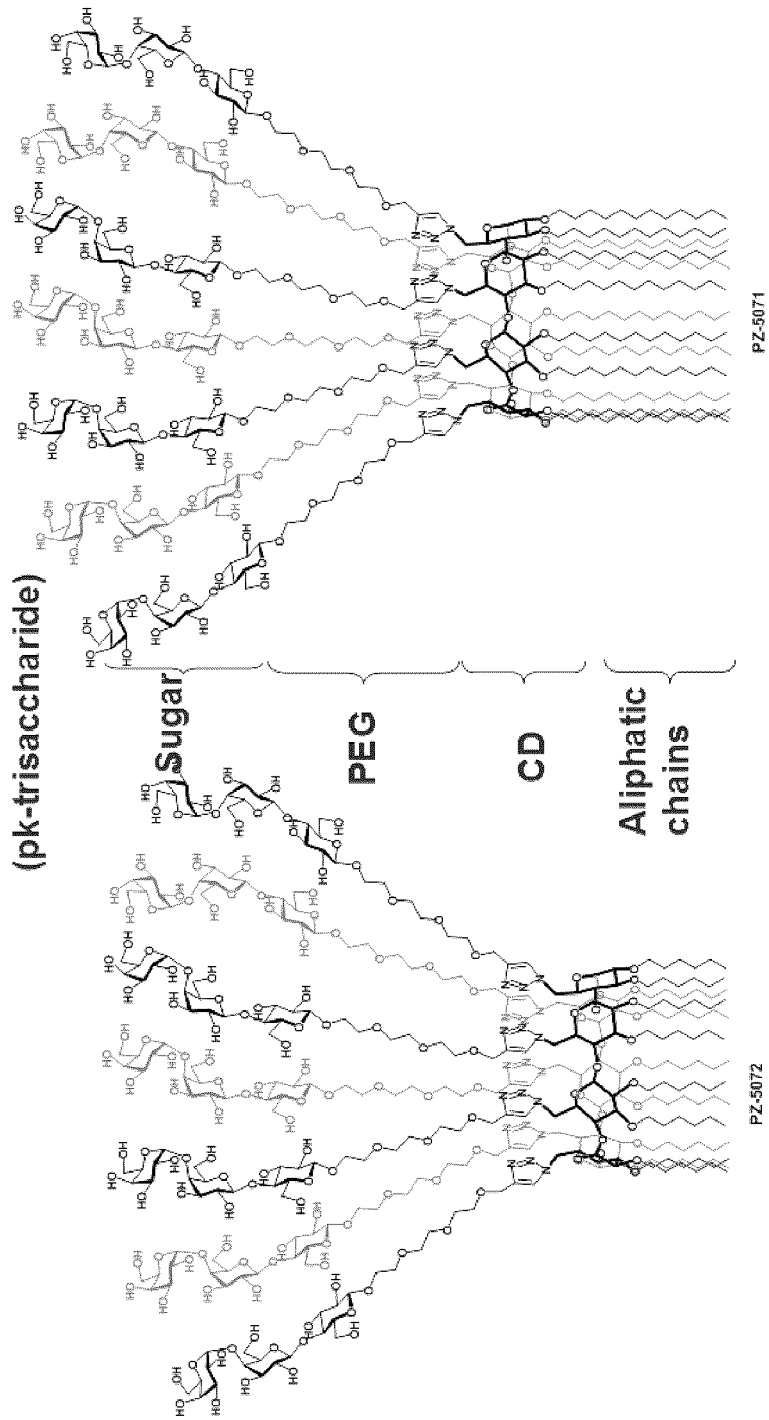
FIG. 27 shows examples of two additional self-assembling glycodendrimers containing a trisacharide epitope (Pk-trisaccharide) recognized by bacterial toxins.

Example 7: Immobilizing Bacterial Toxins on Microtiter Plate Coated with Amphiphilic CD-Based Glycodendrimers Two self-assembling glycodendrimers (PZ-5071 and PZ-5072) containing a Pk-trisaccharide epitope that can be recognized by bacterial toxin (Stx1) are illustrated in FIG. 27.

FIG. 28 shows results of a binding assay of a bacterial toxin, the Shiga-like toxin Stx1 to a microtiter plate precoated with either PZ-5071 or PZ-5072. Both the C6 (PZ-5072) or C12 (PZ-5071) versions of the conjugates were found to bind well with Stx1.

Example 8: Toxicity

Figure 29:
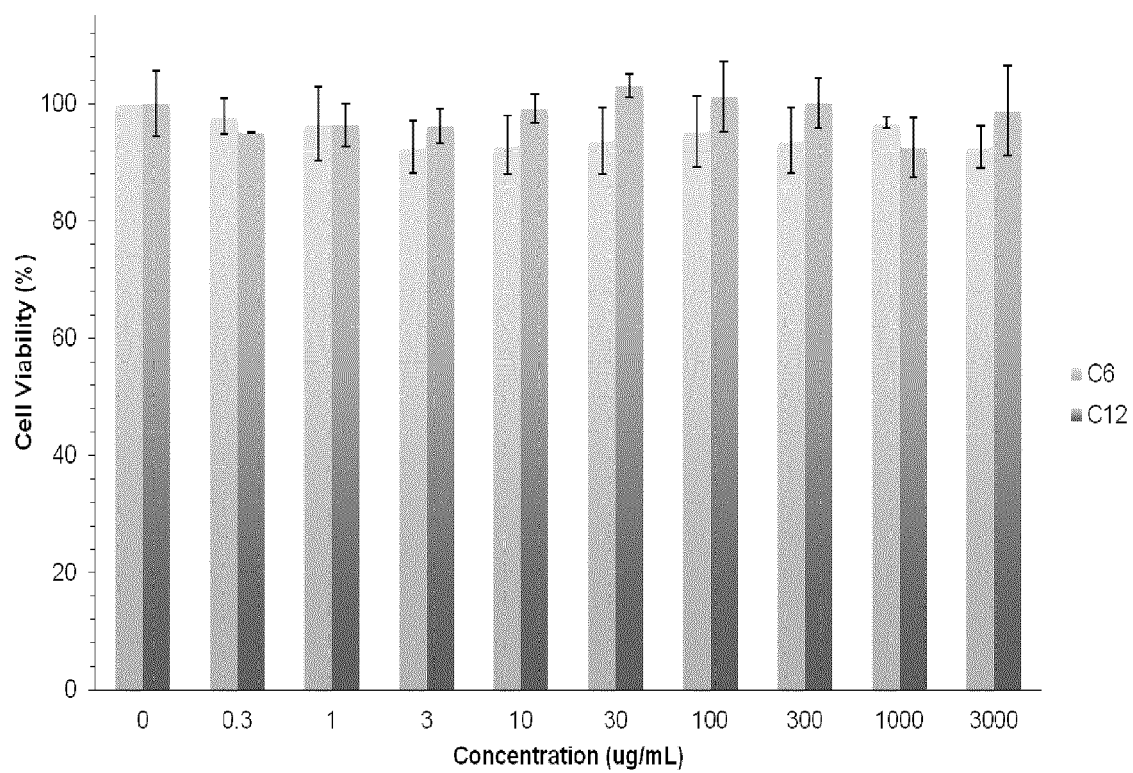
FIG. 29 shows the results of MTT assays of lactose-CD conjugates as described herein comprising $C_6$ and $C_{12}$ alkyl chains.

FIG. 29 shows the results of MTT assays of lactose-CD conjugates as described herein comprising $C_6$ and $C_{12}$ alkyl chains. The results indicate that cell viability is maintained even at increasing concentrations of the conjugate.

Example 9: A Novel Regioselective O-Desilylation Method in CD Chemistry

Previously, Kawahara et al (S. Kawahara, T. Wada and M. Sekine, *J. Am. Chem. Soc.* (1996) 118, 9461-9468) reported that O-tert-butyldimethylsilyl group is sensitive to pH. Thus at pH 2, the O-silyl group could be hydrolyzed to give the O-desilylated product in nucleotide chemistry.

Figure 30:
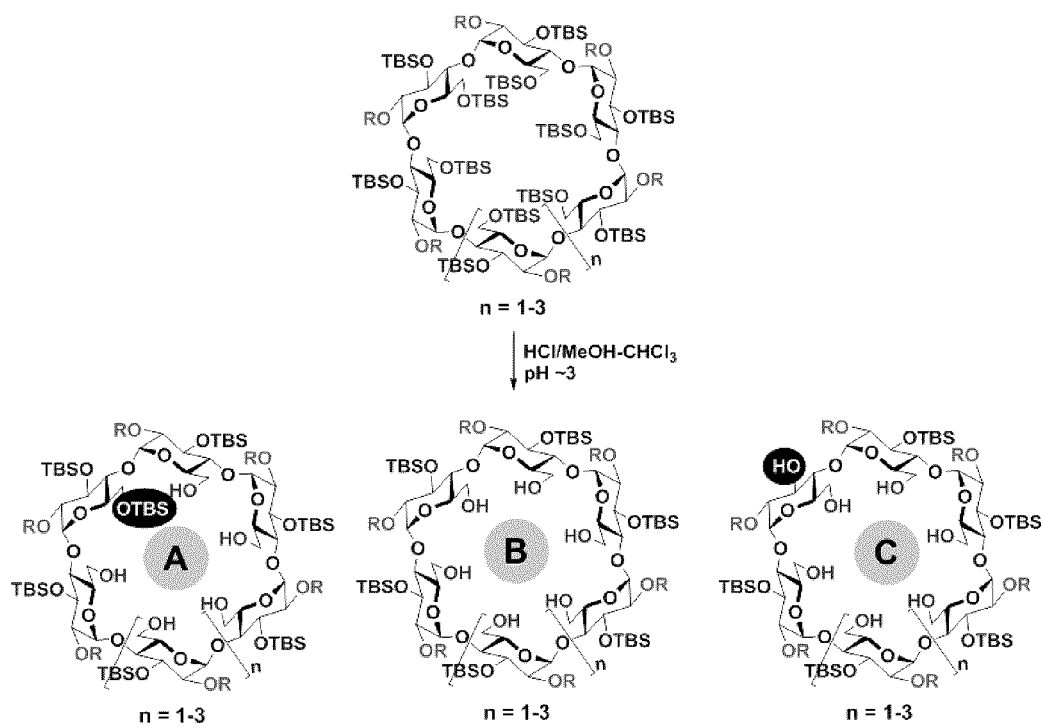
FIGS. 30 and 31 show a novel method related to acid-mediated regioselective O-desilyation in CD chemistry.
Figure 31:
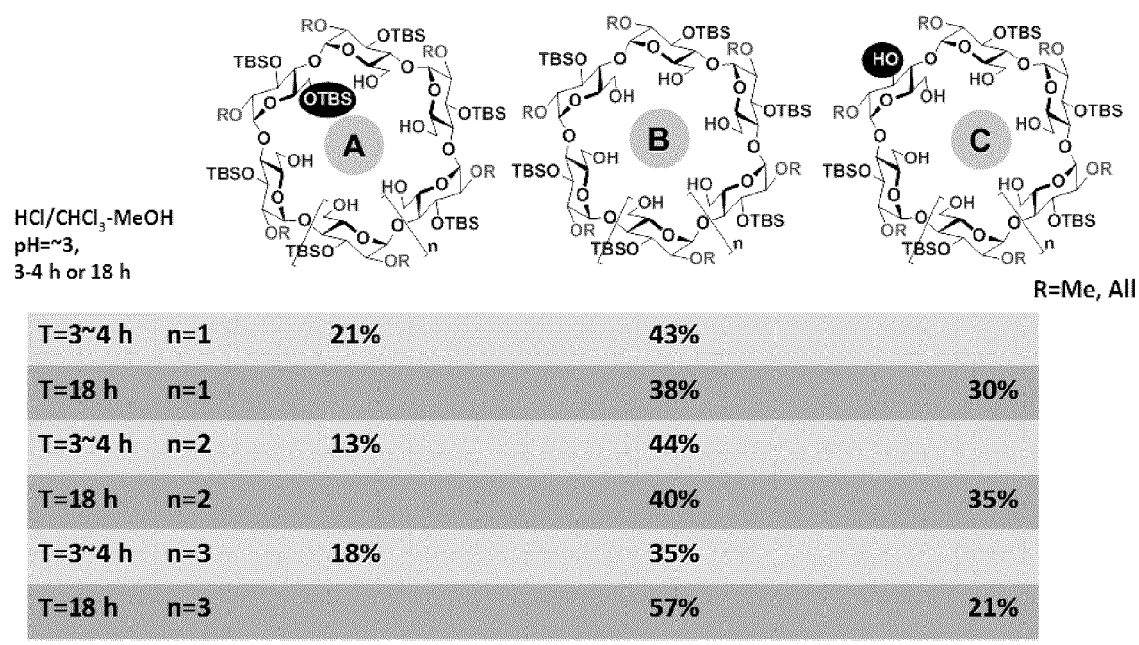

FIGS. 30 and 31 show a novel application of the above method in CD chemistry. In certain embodiments, the acid-catalyzed O-desilylation method is regioselective. The O-silyl groups attached to the primary face of a CD can be regioselectively removed under mild acidic condition (pH 2-4, typically 3) in the presence of O-silyl groups attached to the secondary face of a CD. In addition, by controlling the reaction time, it is possible to obtain the CD derivatives with a complete O-desilylation at the primary face along with CD derivatives with only one silyl group left at the primary face (shorter time, typically 3 hours) or with one more O-silyl group removed at the secondary face (longer time, typically 18 hours). This method could have important applications in CD chemistry as it allows the introduction of multiple functionalities in a CD molecule. Most importantly, this could be potentially used for the efficient synthesis of functionalized amphiphilic CD derivatives.

Example 10

Figure 32:
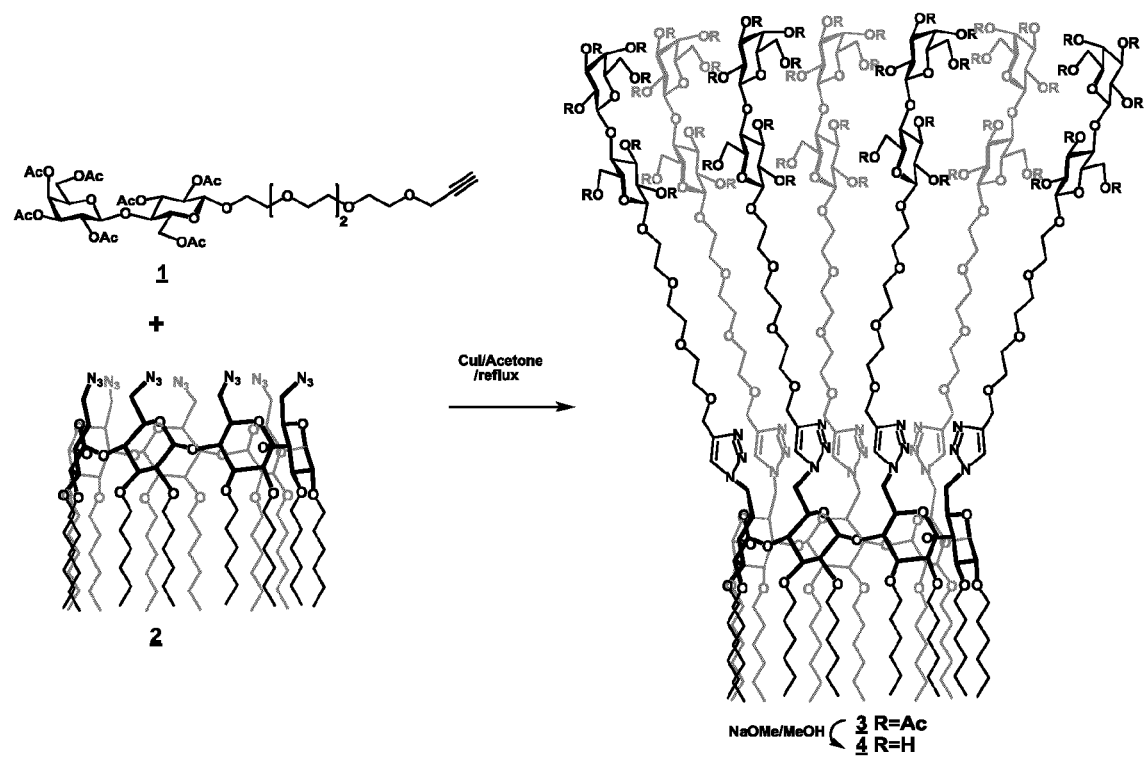
FIG. 32 demonstrates a scheme for synthesizing a glycodendrimer as described herein.

To a solution of the lactosyl derivative (1, 263 mg, 0.33 mmol) and the per-6-azide of β-CD (2, 94 mg, 0.038 mmol) in acetone (20 mL), was added CuI (50 mg) and i-$Pr_2$EtN (100 μL) at room temperature (See FIG. 32). The reaction was refluxed overnight. The mixture was diluted with EtOAc, and washed with a saturated solution of EDTA. The organic phase was separated, dried over $Na_2SO_4$ and evaporated. The residue was purified by column chromatography using a mixture of 4% MeOH—$CH_2Cl_2$ as the eluent to afford the per-acetylated intermediate 269 mg, 88% yield) as white foam. Selected $^1H$ NMR (CDCl$_3$, 400 MHz): $\delta_H$ 7.63 (s, 7H, 7×triazole CH), 5.44 (brs, 7H, 7×H-1_CD), 5.29 (d, 7H, J=3.01, 7×H-4_gal), 5.13 (dd, 7H, J=9.25, 9.25 Hz, 7×H-3_glu), 5.05 (dd, 7H, J=7.93, 10.37 Hz, 7×H-2_gal), 4.91 (dd, 7H, J=3.39, 10.39 Hz, 7×H-3_gal), 4.83 (dd, 7H, J=7.98, 9.46 Hz, 7×H-2_glu), 3.75 (dd, 7H, J=9.48, 9.37 Hz, 7×H-4_glu), 1.51 (m, 28H, 14×O—$CH_2CH_2$ chain), 1.22-1.19 (m, 84H, 14×O—$CH_2CH_2(CH_2)_3$), 0.82 (42H, 14×$CH_3$).

The obtained product (3) was dissolved in anhydrous MeOH (15 mL), and a solution of NaOMe in MeOH (1.5 M, 500 μL) was added, and the mixture was stirred at 50° C. overnight. The mixture was cooled to room temperature, neutralized with dry-ice, and evaporated. The residue was purified by column chromatography on Sephadex LH-20 using MeOH as the eluent to afford the desired compound 4 which was freeze-dried as a white solid (192 mg, 96%). Selected $^1$H NMR (Pyridine-d$_5$, 400 MHz, 373 K): δ$_H$ 7.23 (s, 7H, 7×triazole), 5.92 (d, J=3 Hz, 7H, 7×H-1_CD), 5.02-5.14 (14H, 7×H-6a_CD+7×H-6b_CD), 4.94 (d, 7H, J=7.9 Hz, 7×H-1_gal), 4.81 (d, 7H, J=12.2 Hz, 7×O—CHaHb-triazole), 4.76 (d, 7H, J=12.2 Hz, 7×O—CHaHb-triazole), 4.72 (d, 7H, J=7.9 Hz, 7×H-1_Glu), 1.74-1.97 (m, 28H, 14×O—CH$_2$CH$_2$ chain), 1.31-1.66 (m, 84H, 14×O—CH$_2$CHACH$_2$)$_3$), 1.03 (42H, 14×CH$_3$). HRMS ESI Q-TOF: calcd for [C$_{273}$H$_{483}$N$_{21}$O$_{126}$+3Na]$^+$: 2047.0570. Found: 2047.0532.

Example 11

Figure 33:
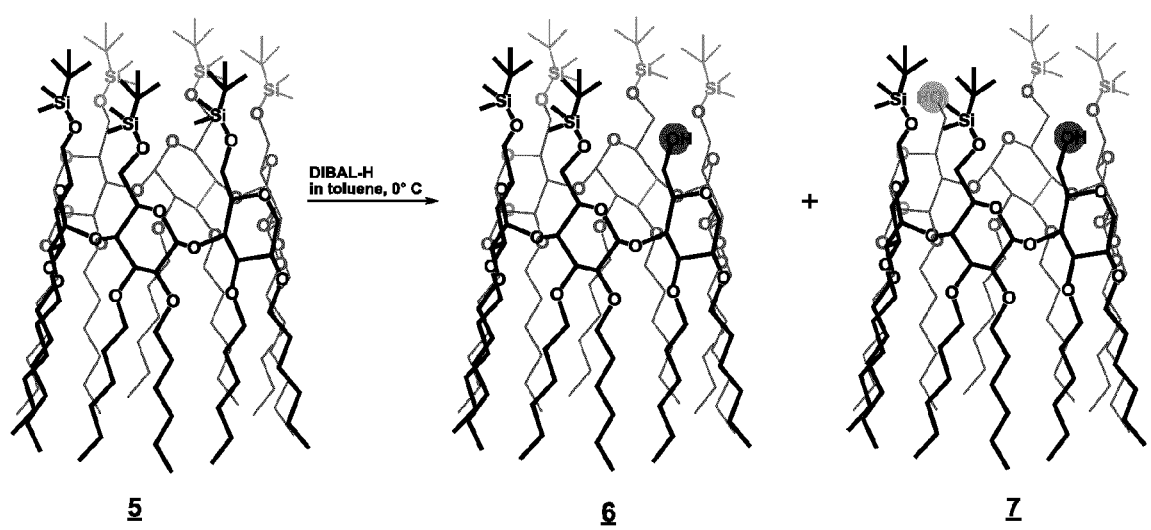
FIG. 33 demonstrates methods for synthesizing a glycodendrimer using DIBAL-H.

The following example is demonstrated in FIG. 33.
Method 1:
DIBAL-H (0.24 mL, 0.24 mmol, 2.5 eq., 0.1 M) was added slowly to a solution of compound 5 (250 mg, 0.094 mmol) in toluene (2.16 mL) at 0° C. The solution was stirred for 2 h and then quenched with 2 N HCl (10 mL) with vigorous stirring for 10 minutes. The toluene phase was taken off and the reaction mixture was diluted with ethyl acetate (20 mL), washed with washed with brine (10 mL) and water (2×15 mL). The organic layer was dried (anhydrous Na$_2$SO$_4$), filtered and concentrated. The crude products were purified by gradient silica gel column chromatography (elution with 2.5% to 3% EtOAc-Hexane) to yield the major product 6 (145 mg, 60% yield) and minor product 7 (67 mg, 28% yield) as colorless solids respectively.
Method 2:
DIBAL-H (0.7 mL, 0.7 mmol, 7.5 eq., 0.3 M) was added slowly to a solution of compound 5 (250 mg, 0.094 mmol) in toluene (1.64 mL) at 0° C. The solution was stirred for 4 h while allowing it to 5° C. and then quenched with 2 N HCl (10 mL) with vigorous stirring for 10 minutes. The toluene phase was taken off and the reaction mixture was diluted with ethyl acetate (20 mL), washed with washed with brine (10 mL) and water (2×15 mL). The organic layer was dried (anhydrous Na$_2$SO$_4$), filtered and concentrated. The crude product was purified by silica gel column chromatography (elution with 3% EtOAc Hexane) to yield diol 7 (192 mg, 84% yield) as colorless.
Selected $^1$H NMR (400 MHz, CDCl$_3$) data for 6: δ 5.34 (d, 1H, J=3.4 Hz, H-1), 5.33 (d, 1H, J=3.4 Hz, H-1), 5.18 (d, 1H, J=3.5 Hz, H-1), 5.10 (d, 1H, J=3.2 Hz, H-1), 5.07 (d, 1H, J=3.0 Hz, H-1), 4.99 (d, 1H, J=3.1 Hz, H-1). HRMS ESI Q-TOF: Calcd for [C$_{138}$H$_{274}$O$_{30}$Si$_5$+Na]$^+$: 2574.8654; found: 2574.8673.
Selected $^1$H NMR (400 MHz, CDCl$_3$) data for 7: δ 5.45 (d, 2H, J=3.8 Hz, 2×H-1), 5.01 (d, 2H, J=3.4 Hz, 2×H-1), 4.93 (d, 2H, J=3.0 Hz, 2×H-1). HRMS ESI Q-TOF: calcd for [C$_{132}$H$_{260}$O$_{30}$Si$_4$+Na]$^+$: 2460.7789; found: 2460.7729.

Example 12

Figure 34:
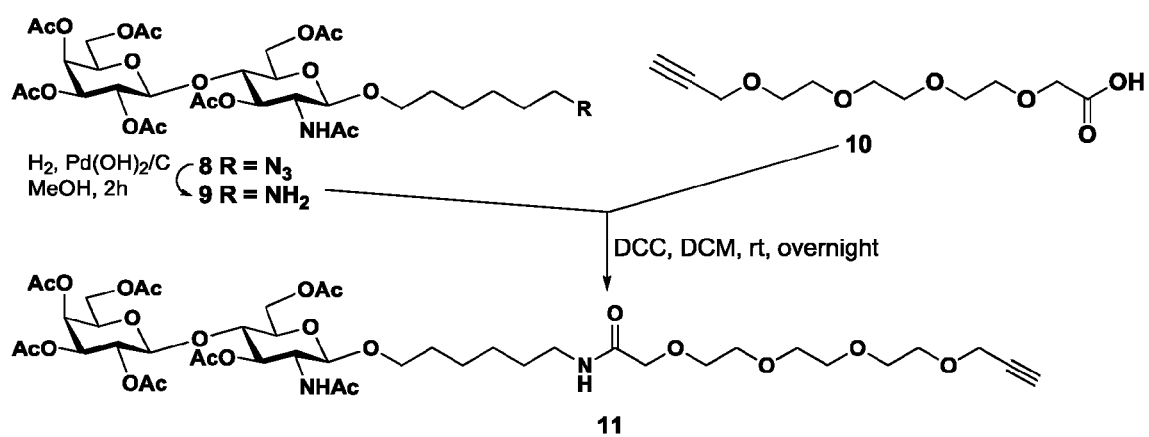
FIG. 34 demonstrates a scheme for synthesizing compound 11.

Compound 8 (150 mg, 0.197 mmol) was dissolved in MeOH (6 mL) and Pd(OH)$_2$/C (20%, 20 mg) was added (See FIG. 34). The reaction mixture was degassed in vacuum and filled with hydrogen atmosphere. After stirring for 1 h, the reaction mixture was filtered off and concentrated. The residue was dissolved in anhydrous CH$_2$Cl$_2$ (6 mL), and the acid 10 (97 mg, 0.394 mmol) was added. The mixture was cooled to 0° C., and DCC (81 mg, 0.393 mmol) were added under argon. The reaction was stirred overnight. The solvent was removed under reduced pressure, and the residue was purified by column chromatography using a gradient of MeOH:CH$_2$Cl$_2$ (1:100 to 1:30) to afford desired product 11 (152 mg, 80% over two steps). Selected $^1$H NMR (400 MHz, CDCl$_3$): δ 7.03 (dd, J=12.3, 6.3 Hz, 1H, —CH$_2$NHCO—), 5.35 (dd, J=3.4, 1.0 Hz, 1H, H-4_Gal), 5.12 (dd, J=8.2, 1.5 Hz, 1H, H-3_Gal), 4.49 (d, J=7.9 Hz, 1H, H-1_Gal), 4.46 (d, J=7.7 Hz, 1H, H-1_GluN). HRMS ESI-QTOF: calcd for m/z for [C$_{43}$H$_{66}$N$_2$O$_{22}$+Na]$^+$985.3999. Found 985.4013.

Example 13

Figure 35:
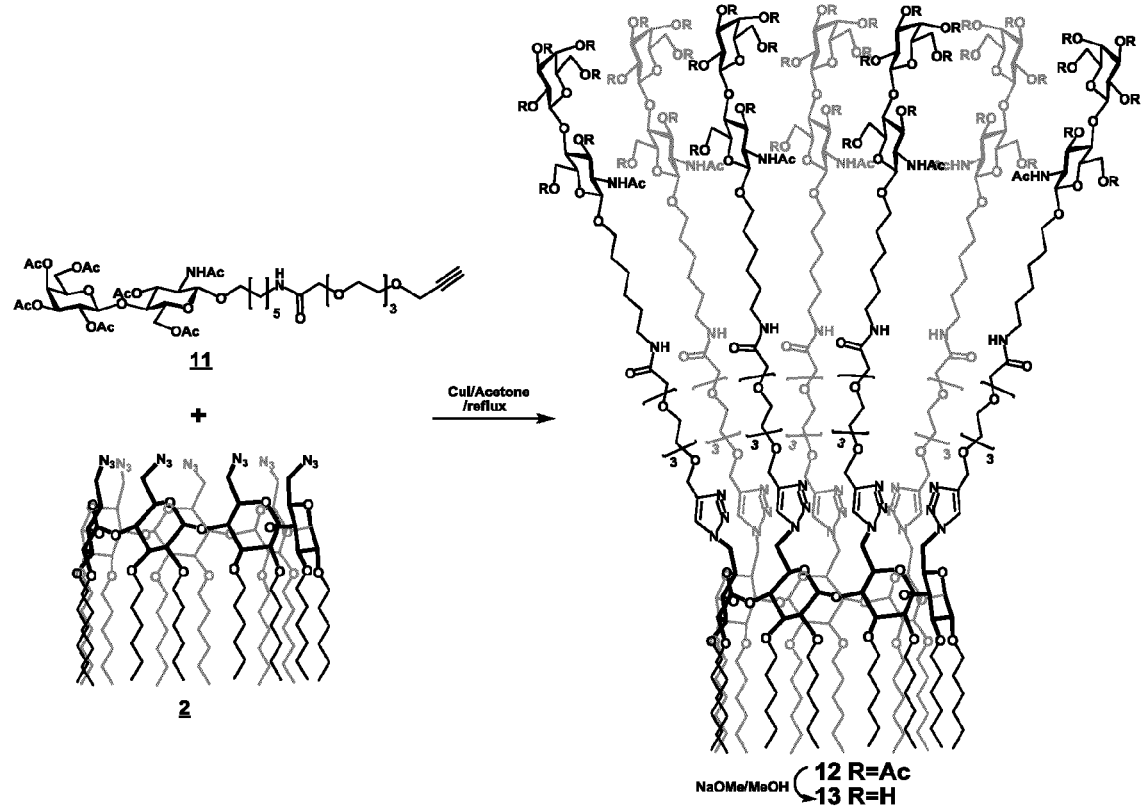
FIG. 35 demonstrates a scheme for synthesizing a glycodendrimer as described herein.

To a solution of compound 11 (110 mg, 0.152 mmol) and per-6-azide of β-CD (2, 40 mg, 0.016 mmol) in acetone (6 ml), was added CuI (20 mg) and i-Pr$_2$EtN (50 μl, 0.09 mmol) under argon atmosphere, and the mixture was heated to reflux overnight (See FIG. 35). The mixture was diluted with EtOAc, washed with a saturated solution of EDTA. The organic phase was separated, dried over Na$_2$SO$_4$ and evaporated under reduced pressure. The residue was purified by column chromatography on silica gel using a mixture of MeOH:CH$_2$Cl$_2$ (7:93) to afford product 12 (110 mg, 74% yield) as a solid. HRMS ESI-QTOF: calcd for m/z for [C$_{427}$H$_{693}$N$_{35}$O$_{182}$+3×H]$^{3+}$ 3075.5422. Found: 3075.5276.
The per-O-acetylated compound 12 (30 mg, 0.00325 mmol) was dissolved in anhydrous methanol (2 mL), and a solution of NaOMe in MeOH (1.5 M, 2 drops) was added at room temperature. The reaction mixture was stirred for 6 hours. Dry ice was added to adjust the pH of the solution to be 7-8. The solvent was removed under reduced pressure, and the residue was purified by column chromatography on Sephadex LH-20 using MeOH as the eluent to afford compound 13 which was freeze-dried (15 mg, 62% yield). Selected $^1$H NMR (600 MHz, D$_2$O): δ 8.03 (s, 7H, H-Triazol), 5.43 (br s, 7H, 7×H-1_CD), 4.62-4.37 (m, 14H, 7×H-1_Gal+7×H-1_GlcNAc), 2.04 (s, 21H), 1.54-1.33 (br m, 168H, 14×OCH$_2$(CH$_2$)$_4$CH$_3$+7×OCH$_2$(CH$_2$)$_4$CH$_2$NH), 0.86 (br m, 42H, 14×CH$_3$). HRMS ESI-QTOF: calcd for m/z for [C$_{343}$H$_{609}$N$_{35}$O$_{140}$+4×Na]$^{4+}$: 1887.7795. Found: 1887.7668.

Example 14

Figure 36:
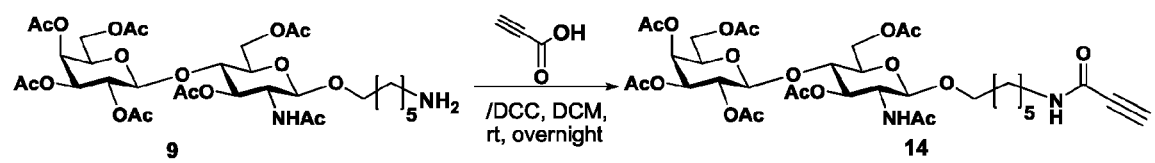
FIG. 36 demonstrates a scheme for synthesizing compound 14.

Compound 9 was coupled with propiolic acid in CH$_2$Cl$_2$ in a similar manner as above using DCC as the reagent to afford compound 14 in 82% yield (See FIG. 36). Selected $^1$H NMR (400 MHz, CDCl$_3$): δ6.61 (dd, J=5.6, 5.6 Hz, 1H, —(CH$_2$)$_6$NHCO—), 4.49 (d, J=7.9 Hz, 1H, H-1_Gal), 4.44 (d, J=7.6 Hz, 1H, H-1_GlcNAc), 2.84 (s, 1H, HCCCONH). HRMS ESI-QTOF: calcd m/z for [C$_{35}$H$_{50}$N$_2$O$_{18}$+Na]$^+$: 809.2951. Found: 809.2958.

Example 15

Figure 37:
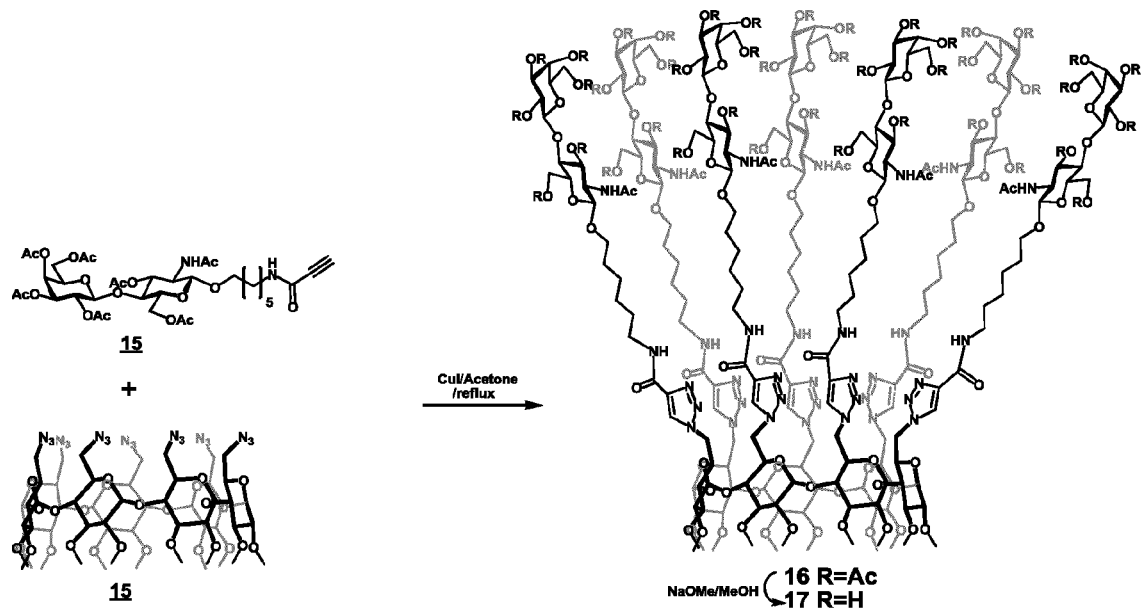
FIG. 37 demonstrates a scheme for synthesizing a glycodendrimer as described herein.

Compound 14 (44 mg, 0.056 mmol) was coupled with compound 15 (10.9 mg, 0.0073 mmol) in acetone (5 ml) using CuI (9.65 mg, 0.051 mmol) as a catalyst and i-Pr$_2$EtN (17.7 ul, 0.101 mmol) as a base (See FIG. 37). Compound 16 (47 mg, 92% yield) was isolated as a colorless oil. Selected $^1$H NMR (400 MHz, Acetone-d$_6$): δ 8.29 (s, 7I-1, 7×Triazol), 7.78 (t, J=5.6 Hz, 7H, 7×—O(CH$_2$)$_6$NHCO—), 7.34 (d, J=9.2 Hz, 7H, 7×NHAc), 4.82 (d, J=7.7 Hz, 7H, 7×H-1_Gal), 4.66 (d, J=8.4 Hz, 7H, 7×H-1_GlcNAc).
Compound 16 (23 mg, 0.00328 mmol) was deacetylated in anhydrous methanol (2 mL) with a solution of NaOMe in MeOH (1.5 M, 2 drops) at room temperature. After stirring for 6 hours, the desired compound 17 was purified by reverse column chromatography on C18 silica gel (15 mg, yield 88%). Selected $^1$H NMR (400 MHz, D$_2$O): δ 8.35 (s, 7H, 7×triazol), 5.40 (brs, 7H, 7×H-1_CD), 4.60-4.31 (m, 21H, 7×H-6a_CD+7×H-1_Gal+7×H-1_GlcNAc). HRMS ESI-QTOF: calcd m/z for $[C_{217}H_{357}N_{35}O_{112}+2\times Na]^{2+}$: 2645.6550. Found: 2645.6537.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. An amphiphilic cyclodextrin-based compound of the formula II:

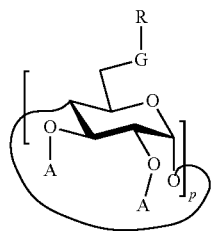

(II)

wherein

R is a hydrophilic group;

G is a linker, wherein G comprises a polyethylene glycol —(CHR'CH$_2$O$_2$)$_n$— where R' is H or CH$_3$ and n is 1 to 20, or G is an alkyl group substituted with (CHR'CH$_2$O$_2$)$_n$— where R' is H or CH$_3$ and n is 1 to 20;

each A is an aliphatic group; and p is 6 to 8.

2. The compound of claim 1, wherein R is a sugar.

3. The compound of claim 2, wherein the sugar is lactose.

4. The compound of claim 1, wherein G further comprises a functional group.

5. The compound of claim 4, wherein the functional group is 1,2,3-triazole.

6. The compound of claim 1, wherein G comprises an amide group.

7. The compound of claim 1, wherein n is 4.

8. The compound of claim 1, wherein p is 7.

9. The compound of claim 1, wherein the aliphatic group is a C$_3$ to C$_{18}$ alkyl group.

10. The compound of claim 9 wherein the aliphatic group is a C$_6$ alkyl group.

11. A drug carrier comprising the compound of claim 1.

12. A method of drug delivery comprising administering the compound of claim 1, together with the drug, to a subject in need thereof.

13. A method of treating bacterial infections by administering the compound of claim 1 wherein R is a sugar moiety, or a linker bearing a sugar moiety, and wherein said sugar moiety is lactose.

* * * * *